(12) United States Patent
Hallberg et al.

(10) Patent No.: US 8,193,324 B2
(45) Date of Patent: Jun. 5, 2012

(54) CONTINUOUS COUNTER-CURRENT ORGANOSOLV PROCESSING OF LIGNOCELLULOSIC FEEDSTOCKS

(75) Inventors: Christer Hallberg, Vancouver (CA); Donald O'Connor, Delta (CA); Michael Rushton, West Vancouver (CA); Edward Kendall Pye, Burnaby (CA); Gordon Gjennstad, Burnaby (CA); Alex Berlin, Burnaby (CA); John Ross MacLachlan, Burnaby (CA); Raymond Ma, Burnaby (CA)

(73) Assignee: Lignol Innovations Ltd., Burnaby (CA)

( * ) Notice: Subject to any disclaimer, the term of this patent is extended or adjusted under 35 U.S.C. 154(b) by 635 days.

(21) Appl. No.: 12/324,311

(22) Filed: Nov. 26, 2008

(65) Prior Publication Data

US 2009/0118477 A1 May 7, 2009

Related U.S. Application Data

(63) Continuation-in-part of application No. 12/016,932, filed on Jan. 18, 2008, and a continuation-in-part of application No. 11/839,378, filed on Aug. 15, 2007, now abandoned.

(60) Provisional application No. 60/941,220, filed on May 31, 2007.

(51) Int. Cl.
| | |
|---|---|
| *C07G 1/00* | (2006.01) |
| *C08H 7/00* | (2011.01) |
| *C08L 97/00* | (2006.01) |
| *C12P 1/00* | (2006.01) |
| *C12P 19/14* | (2006.01) |
| *D21C 11/00* | (2006.01) |

(52) U.S. Cl. ............ 530/500; 435/41; 435/99; 162/14
(58) Field of Classification Search .............. 435/41, 435/99; 530/500; 162/14
See application file for complete search history.

(56) References Cited

U.S. PATENT DOCUMENTS

| 5,730,837 A | 3/1998 | Black et al. |
|---|---|---|
| 5,788,812 A * | 8/1998 | Agar et al. ............. 162/16 |
| 5,879,463 A | 3/1999 | Proenca |
| 5,916,780 A | 6/1999 | Foody et al. |
| 8,067,193 B2 | 11/2011 | Hughes et al. |
| 2007/0259412 A1 * | 11/2007 | Belanger et al. ............ 435/161 |

FOREIGN PATENT DOCUMENTS

| CA | 1201115 | 2/1986 |
|---|---|---|
| CA | 1230592 | 12/1987 |
| CA | 2419658 | 3/2002 |
| WO | 2008/008793 A2 | 1/2008 |

OTHER PUBLICATIONS

Meiyun Zhang et al. "Removal of Residual Lignin of Ethanol-Based Organosolv Pulp by an Alkali Extraction Process" Journal of Applied Polymer Science, vol. 106, 630-636 (2007).*
New Zealand Office Action date Oct. 29, 2010 received on corresponding New Zealand patent application No. 580751.
Chinese Office Action date Feb. 24, 2011 received on corresponding Chinese patent application No. 2011022100348110.
Pan et al., Biotechnology and Bioengineering, 2005, vol. 90(4), pp. 473-481, Wiley Periodicals Inc.

\* cited by examiner

*Primary Examiner* — Jon P Weber
*Assistant Examiner* — Thane Underdahl
(74) *Attorney, Agent, or Firm* — Gowling Lafleur Henderson LLP

(57) ABSTRACT

A modular process for organosolv fractionation of lignocellulosic feedstocks into component parts and further processing of said component parts into one or more of a de-lignified cellulose stream, a sugar stream, small-chain alcohol streams and four structurally distinct classes of lignin derivatives. The modular process comprises a first processing module configured for digesting lignocellulosic feedstocks with an organic solvent thereby producing a cellulosic solids fraction and a liquid fraction, a second processing module configured for recovering small-chain alcohols and optionally a first class of lignin derivatives from the cellulosic solids fraction, a third processing module configured for recovering from the liquid fraction at least one of a second class and a third class of lignin derivatives or mixtures thereof, and waste stream comprising a fourth class of lignin derivatives. The fourth processing module may optionally recover the fourth class of lignin derivatives.

11 Claims, 13 Drawing Sheets

Fig. 11
(a)
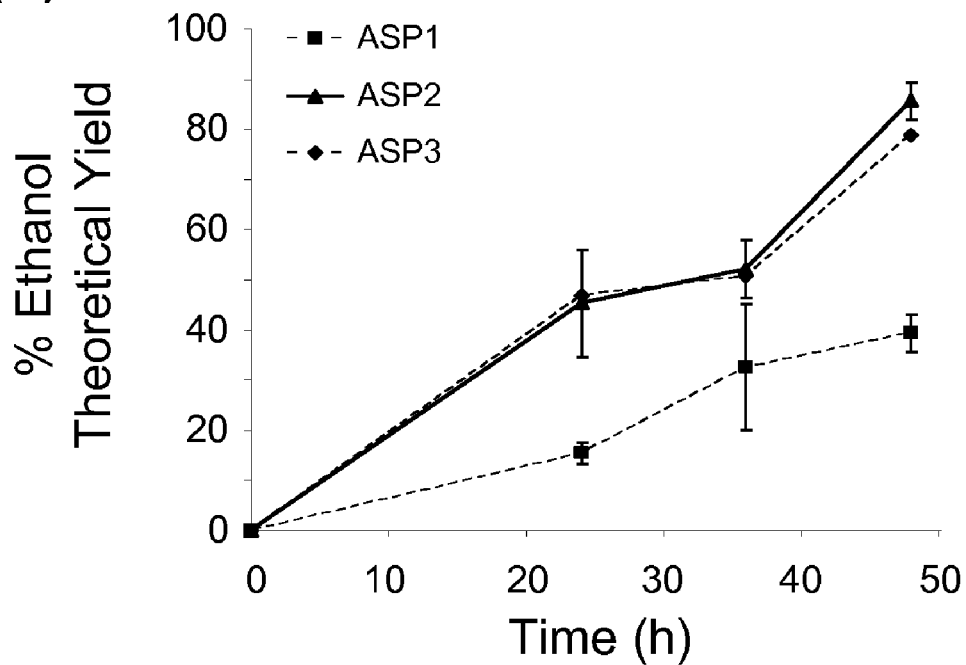
(b)
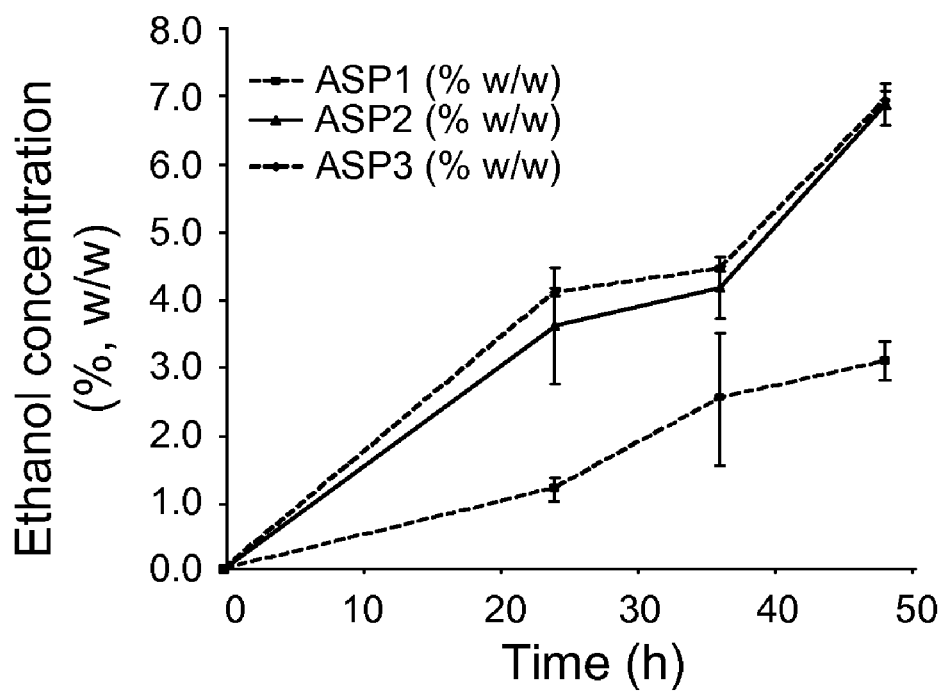

Fig. 12
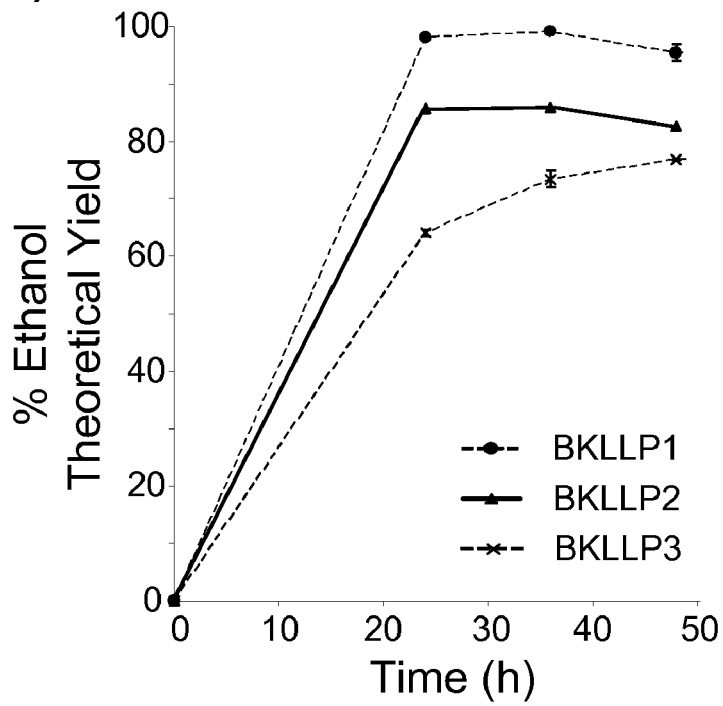
(a)
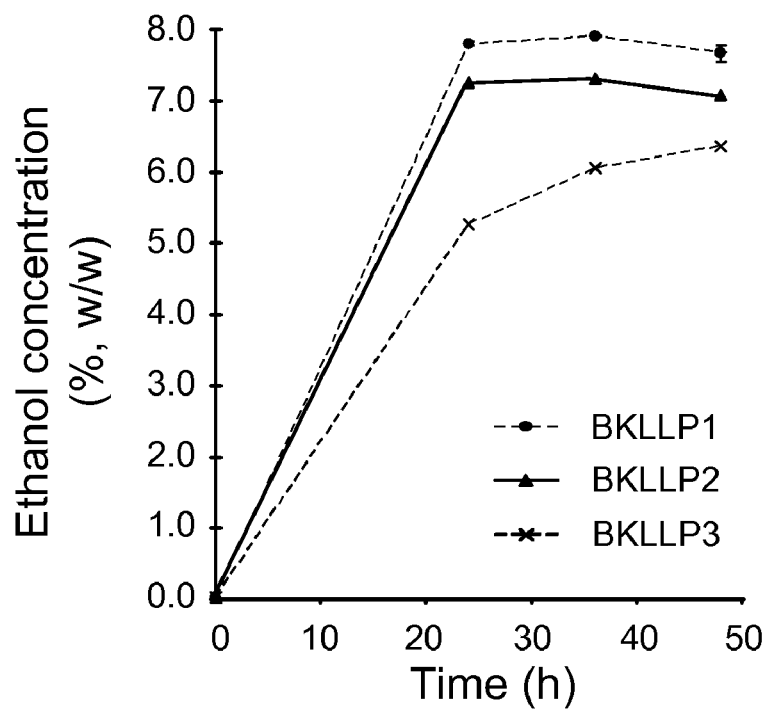
(b)

Fig. 13
(a)
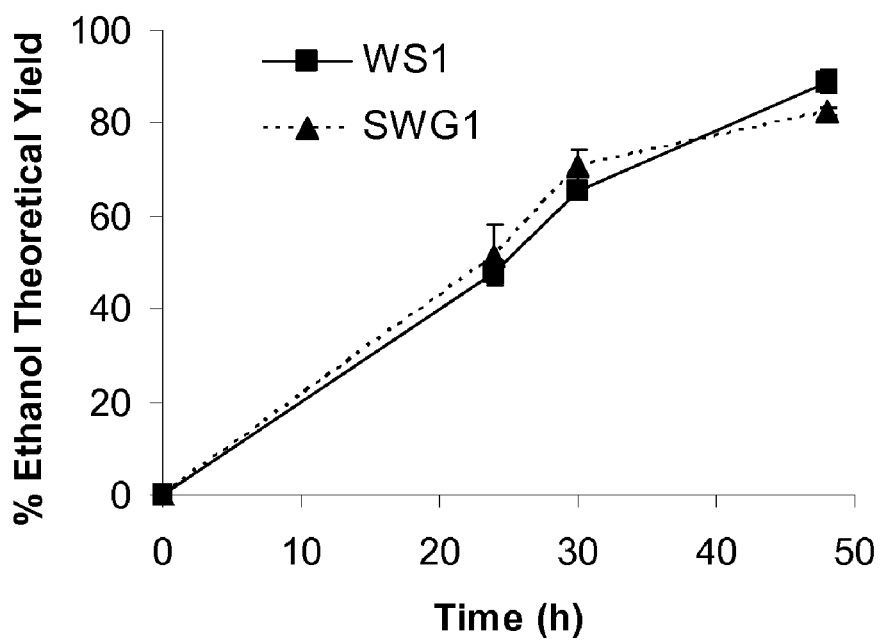
(b)
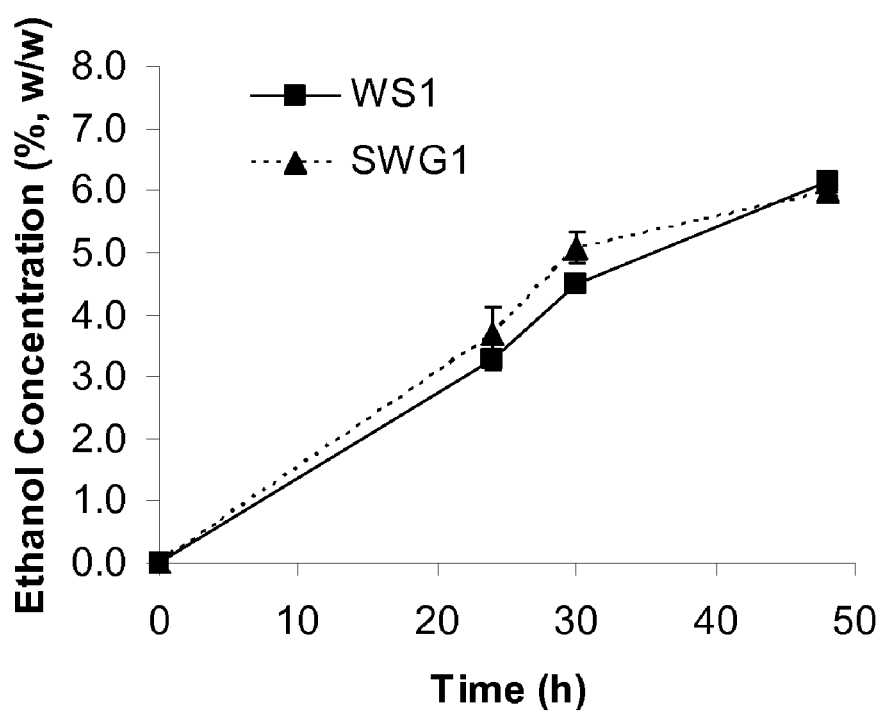

CONTINUOUS COUNTER-CURRENT ORGANOSOLV PROCESSING OF LIGNOCELLULOSIC FEEDSTOCKS

CROSS-REFERENCE TO RELATED APPLICATIONS

This application is a continuation-in-part of application Ser. No. 12/016,932 filed Jan. 18, 2008, which is a continuation-in-part of application Ser. No. 11/839,378 filed Aug. 15, 2007 and claims benefit of Provisional Application No. 60/941,220 filed May 31, 2007.

FIELD OF THE INVENTION

This invention relates to fractionation of lignocellulosic feedstocks into component parts. More particularly, this invention relates to processes, systems and equipment configurations for recyclable organosolv fractionation of lignocellulosic material for controllable and manipulable production and further processing of lignins, monosaccharides, oligosaccharides, polysaccharides and other products derived therefrom.

BACKGROUND OF THE INVENTION

Industrial processes for production of cellulose-rich pulps from harvested wood are well-known and typically involve the steps of physical disruption of wood into smaller pieces and particles followed by chemical digestion under elevated temperatures and pressures to dissolve and separate the lignins from the constituent cellulosic fibrous biomass. After digestion has been completed, the solids comprising the cellulosic fibrous pulps are separated from the spent digestion liquids which commonly referred to as black liquors and typically comprise organic solvents, solubilized lignins, solid and particulate monosaccarides, oligosaccharides, polysaccharides and other organic compounds released from the wood during the chemical digestion. The cellulosic fibrous pulps are typically used for paper manufacturing while the black liquors are usually processed to recover the heat value in the soluble lignins and for recovery, purification and recycling of the solvents.

During the past two decades, those skilled in these arts have recognized that lignocellulosic materials including harvested gymnosperm and angiosperm substrates exemplified by chips and sawdust, woody undercuttings and debris from forest plantations, annual and perennial field crop residues, bagasse and other like types of herbaceous fibrous biomass, waste paper wood products, waste materials and debris from wood-processing operations, and the like, can be potentially fractionated using biorefining processes incorporating organosolv digestion systems, into multiple useful component parts that can be separated and further processed into high-value products such as fuel ethanol, lignins, furfural, acetic acid, purified monosaccharide sugars among others (Pan et al., 2005, Biotechnol. Bioeng. 90: 473-481; Pan et al., 2006, Biotechnol Bioeng. 94: 851-861; Berlin et al., 2007, Appl. Biochem. Biotechnol. 136-140:267-280; Berlin et al., 2007, J. Chem. Technol Biotechnol. 82: 767-774). Organosolv pulping processes and systems for lignocellulosic feedstocks are well-known and are exemplified by the disclosures in U.S. Pat. Nos. 4,941,944; 5,730,837; 6,179,958; and 6,228,177. Although it appears that biorefining using organosolv systems has considerable potential for large-scale fuel ethanol production, the currently available processes and systems are not yet economically feasible because they require expensive pretreatment steps and currently produce only low-value co-products (Pan et al., 2006, J. Agric. Food Chem. 54: 5806-5813; Berlin et al., 2007, Appl. Biochem. Biotechnol. 136-140:267-280; Berlin et al., 2007, J. Chem. Technol Biotechnol. 82: 767-774).

SUMMARY OF THE INVENTION

The exemplary embodiments of the present invention relate to systems, processes and equipment configurations for biorefining of lignocellulosic feedstocks into component parts which are then subsequently separated. The separated component parts are further selectively, controllably and manipulably processed.

According to one exemplary embodiment of the present invention, there is provided a modular biorefining processing system for receiving therein and fractionating a lignocellulosic feedstock into component parts, separating the component parts into at least a solids fraction and a liquids fraction, and then separately processing the solids and liquids fractions to further produce useful products therefrom. Suitable modular biorefining processing systems of the present invention comprise at least:

a first module comprising a plurality of equipment configured for: (a) receiving and processing lignocellulosic fibrous feedstocks, then (b) commingling under controlled temperature and pressure conditions the processed feedstocks with suitable solvents configured for physico-chemically disrupting the lignocellulosic feedstock into a solids fraction comprising mostly cellulosic pulps and a liquid fraction comprising spent solvents containing therein at least lignins, lignin-containing compounds, monosaccharides, oligosaccharides and polysaccharides, dissolved and suspended solids comprising hemicelluloses and celluloses and other organic compounds, and (c) providing a first output stream comprising the cellulosic solids fraction having a plurality of a first class of structurally distinct lignin derivatives integrally but incidentally associated therewith, and a second output stream comprising a black liquor liquids fraction comprising spent organic solvents and solubilized extractives therein comprising the three additional structurally distinct classes of lignin derivatives.

a second processing module configured for receiving and processing the cellulosic solids fraction, and recovering therefrom at least a processed cellulose pulp stream;

a third processing module configured for separating the black liquor liquids fraction into a partially de-lignified liquid fraction and a first solids fraction comprising at least one of a plurality of a second class of structurally distinct lignin derivatives and a plurality of a third class of structurally distinct lignin derivatives, and recovering from the partially de-lignified liquid fraction at least a portion of the organic solvent and a waste stream comprising a plurality of a fourth class of structurally distinct lignin derivatives; and a fourth processing module configured for recovery of a first semi-solid waste material therefrom the waste stream.

According to another exemplary embodiment, the second processing module may be configured for receiving and de-lignifying the cellulosic solids fraction with a suitable bleaching process and recovering a de-lignified cellulose pulp stream. Suitable bleaching processes are exemplified by elemental chlorine-free bleaching processes and total chlorine-free bleaching processes. The de-lignified cellulose pulp may be recovered for use as a highly purified cellulose feedstock in other industrial applications. Alternatively, the cellulose pulp may be enzymatically hydrolyzed to produce a carbohydrates sugar stream that can be recovered for other industrial applications. Alternatively, the carbohydrates sugar stream may fermented to produce short-chain alcohols that are refinable into fuel-grade alcohols and industrial-grade alcohols exemplified by ethanol and butanol.

According to another exemplary embodiment, the second processing module may be configured for enzymatically hydrolyzing the cellulosic solids fraction to produce a carbohydrates sugar stream that fermented to produce a fermentation beer from which is recovered short-chain alcohols and a fluid waste stream. The short-chain alcohols are refinable into fuel-grade alcohols and industrial-grade alcohols exemplified by ethanol and butanol. The plurality of the first class of lignins derivatives may be optionally recovered from the fluid waste stream.

Another exemplary embodiment relates to process and systems modifications to the second processing module to enable recovery at least a portion of enzymes provided for enzymatic hydrolysis of the cellulosic solids stream, and for conditioning and recycling the recovered enzymes for additional hydrolysis of fresh cellulosic solids streams. Other exemplary embodiments relate to process and systems modifications configured for recovery of at least a portion of the fermenting microorganisms from fermentation vessels, conditioning and recycling of the fermenting microorganisms for additional fermentations of fresh carbohydrates sugar streams hydrolysed from the cellulosic solids stream.

Other exemplary embodiments of the present invention relate to alternative process and systems configurations for the third processing module for separation and recovery of one or more pluralities of structurally distinct classes of lignins from the black liquor liquids fraction, and for recovery of a fluid waste stream comprising a plurality of the fourth class of structurally distinct lignin derivatives. The fourth class of structurally distinct lignin derivatives are optionally recovered in the fourth processing module.

Another exemplary embodiment relates to an optional fifth processing module configured to receive therein at least one waste stream from at least one of the second, third and fourth processing module, and to convert the waste stream into a biogas, a fluid effluent and mineral solids.

BRIEF DESCRIPTION OF THE DRAWINGS

The present invention will be described in conjunction with reference to the following drawings in which:

FIG. 11 shows plots illustrating the simultaneous saccharification and fermentation (SSF) of organosolv-pretreated aspen (*Populus tremula*) chips: (a) % theoretical yield of ethanol produced from the resultant aspen pulps vs. time, and (b) the ethanol concentration in beers vs. time, produced during SSF of the aspen pulps;

FIG. 12 shows plots illustrating the SSF of organosolv-pretreated British Columbian beetle-killed lodgepole pine (*Pinus contorta*) chips: (a) % theoretical yield of ethanol produced from the resultant beetle-killed lodgepole pine pulps vs. time, and (b) the ethanol concentration in beers vs. time, produced during SSF of the resultant beetle-killed lodgepole pine pulps; and FIG. 13 shows plots illustrating the simultaneous saccharification and fermentation (SSF) of organosolv-pretreated wheat straw and switchgrass lignocellulosic feedstocks: (a) % theoretical yield of ethanol produced from the resultant cellulosic pulps vs. time, and (b) the ethanol concentration in beers vs. time, produced during SSF of the cellulosic pulps.

DETAILED DESCRIPTION OF THE INVENTION

Figure 1:
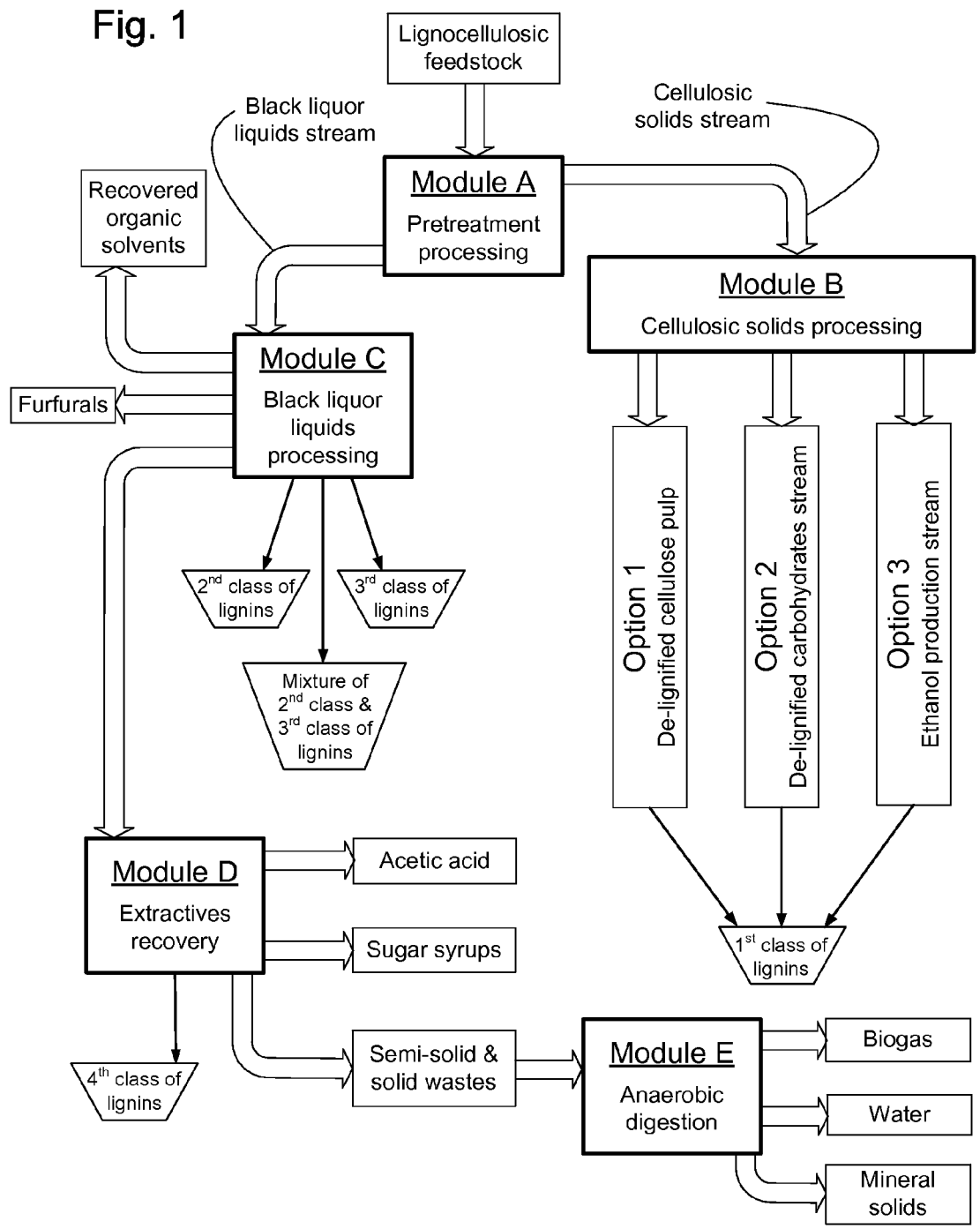
FIG. 1 is a schematic flowchart showing various exemplary embodiments of the present invention for modular biorefinery processing of lignocellulosic feedstocks for recovery of different product streams and various structural classes of lignin derivatives.

Exemplary embodiments of the present invention relate to biorefining systems, processes and equipment configurations for receiving and controllably commingling lignocellulosic feedstocks with organic solvents, thereby fractionating the lignocellulosic feedstocks into component parts which are then subsequently separated. The separated component parts are further selectively, controllably and manipulably processed. The exemplary embodiments of the present invention are particularly suitable for separating out the lignocellulosic feedstocks into a cellulosic solids stream comprising cellulose fibers having a plurality of a first class of structurally distinct lignin derivatives that are integrally but incidentally associated therewith, and a black liquor liquid stream comprising a mixture of spent organic solvents and solubilized extractives from the lignocellulosic feedstocks. The solubilized extractives include pluralities of three additional structurally distinct classes of lignin derivatives. Also provided are processes and systems for separating the cellulosic solids stream into one or more of a de-lignified cellulose pulp stream and a carbohydrates stream. The processes and systems may be additionally configured for conversion of one or more of the cellulosic solids stream, the de-lignified cellulose pulp stream, and the carbohydrates stream into a short-chain alcohol stream, e.g., an ethanol stream. Also are provided processes and systems for recovery of at least a portion of the organic solvents from the black liquor stream, and optionally, for separating and recovering one or more of the three additional structurally distinct classes of lignin derivatives, and further separating therefrom the processed black liquor stream one or more of furfurals, acetic acid, and/or carbohydrates sugar streams.

Those skilled in these arts will understand that biorefining pertains to the integration of biomass conversion processes and equipment to produce multiple products including fuels, chemicals, thermal energy and electrical power from a biomass feedstock. By concurrently producing multiple products, a biorefinery can take advantage of the differences in biomass components and intermediates, and maximize the values derived from different types and qualities of feedstocks. Furthermore, concurrent production of multiple products enables controllable directed manipulation of process subcomponents to preferentially produce more of certain selected products while concurrently producing less of other products.

An exemplary embodiment of the present invention relates to subdividing a biorefinery system into smaller parts (i.e., modules or components) that are interconnected but are configured such that each module can be independently created, and separately and controllably operated. However, the interconnections between the modules enable controllably directed delivery of process inputs into the individual modules, and the controllable egress and transfer of process outputs from the individual modules to other modules. For clarity, each module comprising a biorefinery system according to the present module is configured to receive and process therein at least one input feedstock thereby producing at least two or more product output streams. Each product output stream from one module may be transferred to a second module as an input feedstock wherein it is converted into two or more new product output streams. The configurations of each module and the interconnections between the module enable targetted and controllable recovery of some or all of each product output stream from a selected module, or alternatively, transfer of some or all of each product output stream from the selected module to another module, thereby enabling the modular biorefinery to drive different but integrated functionalities. The exemplary modular biorefineries of the present invention are characterized by functional partitioning into discrete scalable, reusable modules consisting of isolated, self-contained functional elements, rigorous use of well-defined modular interfaces including object-oriented descriptions of module functionality, ease of change to achieve technology transparency and, make use of industry standards for key interfaces. In addition to flexibility in design, modularization of biorefining systems enables additing on additional modules to further process product output streams thereby creating addition product capture opportunities, and also enables by-passing one or more processing modules if so desired.

An exemplary embodiment of a modular biorefinery system according to present invention, for processing lignocellulosic feedstocks may comprise four modules wherein the first module is configured to receive and process therein with a solvent, a lignocellulosic feedstock to produce a cellulosic solids output and a liquid extractives output. The cellulosic solids output from the first module is transferable as a feedstock into a second module wherein the feedstock is converted into a recoverable ethanol stream and a waste stream. The liquid extractives output from the first module is transferrable as as feedstock into a third module wherein a portion of the solvent is recovered from feedstock and recycled back into the first module. The de-solventized feedstock in the third module may be further processed to precipitate and recover therefrom a target extractive product thereby producing a refined liquid product output. The refined liquid product output is transferrable into a fourth module for optional recovery of one or more additional extractives. An optional fifth module may be provided to receive and process therein one or more of the waste stream from the second module, the refined liquid product output from the third module, and one or more product streams from the fourth module.

An exemplary modular processing system of the present invention is shown in FIG. 1 and generally comprises four modules A-D wherein the first module A is configured for receiving and processing lignocellulosic feedstocks with at least one organic solvent whereby the processed lignocellulosic feedstocks are separable into a cellulosic solids fraction comprising cellulose fibers and the first class of lignin derivatives integrally but incidentally associated therewith, and a black liquor liquids fraction comprising spent organic solvents and solubilized extractives therein comprising the three additional classes of lignin derivatives.

The second module B is configurable for receiving the cellulosic solids fraction discharged from the first module A and for recovering therefrom at least one of a cellulose pulp stream, a carbohydrates stream, an ethanol stream, and optionally, the first class of lignin derivatives. The first class of lignin derivatives is integrally associated with the cellulose fibres and originate from native lignin polymers produced during plant growth and development. This first class of lignin derivatives comprises a plurality of relatively very high molecular weight lignin fractions derived during organosolv solubilization of the native lignin polymers during the processing of the lignocellulosic feedstocks in the first module A. This first class of lignin derivatives is referred to hereafter as a very high molecular weight class of lignin derivatives (i.e., VHMW lignin).

The third module C is configurable for receiving the black liquor liquid stream from the first module A and for recovering therefrom at least a portion of the spent organic solvent and at least some of the three additional structurally distinct classes of lignin derivatives. The second class of lignin derivatives comprises a plurality of relatively high molecular weight lignin structures that are released by organosolv solubilization of the native lignin polymers during the processing of the lignocellulosic feedstocks in the first module A. The second class of lignin derivatives is referred to hereafter as a high molecular weight class of lignin derivatives (i.e., HMW lignin). HMW lignin derivatives have a tendency to self-precipitate from the black liquor liquid stream if it is cooled upon egress from the first module A. The third class of lignin derivatives comprises a plurality of relatively medium molecular weight lignin structures that are derived during organosolv solubilization of the native lignin polymers during the processing of the lignocellulosic feedstocks in the first module A, and is referred to hereafter as a medium molecular weight class of lignin derivatives (i.e., MMW lignin). MMW lignin derivatives may be precipitated from the black liquor liquid stream by copious dilution of the black liquor with water. Module C may be optionally configured for co-precipitation of the HMW lignin derivatives with the MMW derivatives by maintaining the black liquor liquid fraction at elevated temperatures while rapidly diluting the black liquor with copious amounts of water, thereby enabling recovery of precipitated solids comprising a mixture of pluralities of HMW lignin derivatives and MMW lignin derivatives. The precipitated HMW lignin derivatives, MMW lignin derivatives, and mixtures of HMW lignin derivatives co-precipitated with MMW lignin derivatives are separable from the processed black liquor liquid streams with standard chemical processing equipment and systems known to those skilled in these arts. Suitable separation equipment is exemplified by decanter centrifuges and filtration systems. Spent organic solvents may be recovered from the de-lignified black liquor solutions by distillation, with concurrent recovery of furfurals if so desired. The resulting stillage comprises extractives and the fourth class of lignin derivatives that are composed of very-low molecular weight lignin structures that are derived during organosolv solubilization of the native lignin polymers during the processing of the lignocellulosic feedstocks in the first module A. The fourth class of lignin derivatives is referred to hereafter as a very low molecular weight class of lignin derivatives (i.e., VLMW lignin). The stillage comprising the processed black liquor remaining after recovery of the organic solvents in the second module C may be further processed in the fourth module D for separation and recovery therefrom of one or more of the extractives solubilized from the lignocellulosic feedstock in the first module A.

The fourth module D is configurable for receiving and separating the stillage from the third module C into one or more of acetic acid, VLMW lignin derivatives, a sugar syrup stream, and a semi-solid/solid waste material.

An additional exemplary embodiment of the present invention relates to an optional fifth module E configurable for receiving therein the semi-solid/solid waste material from the fourth module D and for anaerobically digesting the material into collectible biogas, water and mineral solids components. The fifth module E may also receive therein the processed black liquor stillage from the third module C and for anaerobically digesting the stillage into collectible biogas, water and mineral solids components.

Another additional exemplary embodiment of the present invention relates to an optional sixth module F configurable for receiving therein the sugar syrup stream from the fourth module D, and for fermenting and then distilling therein sugar syrup stream. A 1,3-propanediol component is separable from the distillate. At least a lactic acid component is separable from the stillage separated from the 1,3-propanediol distillage.

Figure 2:
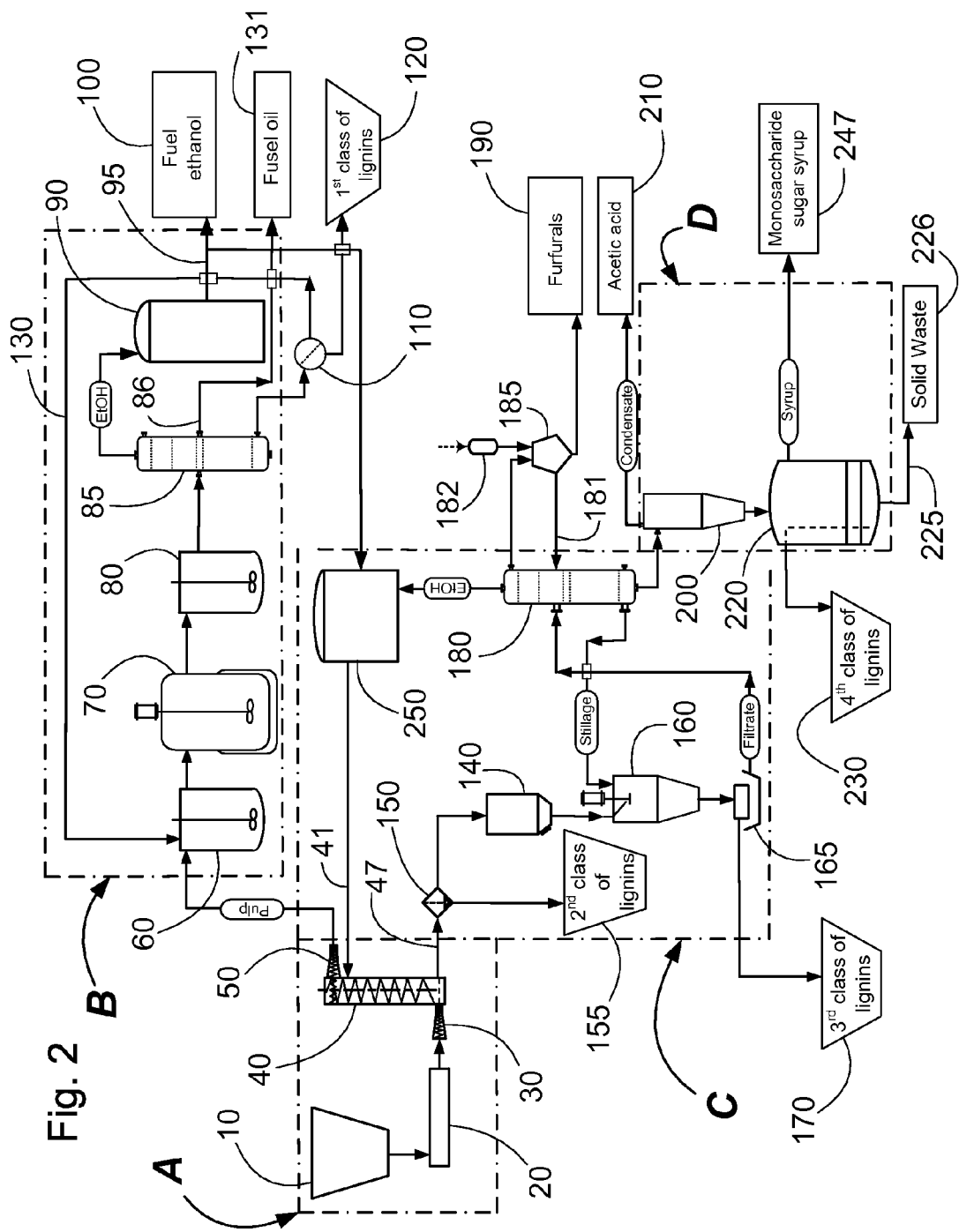
FIG. 2 is a schematic flowchart of an exemplary embodiment of the present invention of a modular continuous counter-flow system for processing a lignocellulosic feedstock.

An illustrative exemplary modular processing system of the present invention in shown in FIG. 2, wherein the first module A is provided with a bin 10 configured for receiving and temporarily storing lignocellulosic feedstocks while continually discharging the feedstock into a conveyance system provided with a separating device 20 configured for removing pebbles, gravel, metals and other debris. A suitable separating device is a screening apparatus. The separating device 20 may be optionally configured for sizing the lignocellulosic feedstock into desired fractions. The processed lignocellulosic feedstock is then conveyed with a first auger feeder 30 into a first end of a digestion/extraction vessel 40 and then towards the second end of the digestion/extraction vessel 40. The vessel 40 is provided with an inlet approximate the second end for receiving a pressurized stream of a suitable heated digestion/extraction solvent which then counterflows against the movement of the lignocellulosic feedstock through the vessel 40 thereby providing turbulence and commingling of the solvent with the feedstock. Alternatively, the inlet for receiving the pressurized stream of heated digestion/extraction solvent may be provided about the first end of the digestion/extraction vessel 40 or further alternatively, interposed the first and second ends of the digestion/extraction vessel 40. It is suitable to use organic solvents for the processes of the present invention. Exemplary suitable organic solvents include methanol, ethanol, propanol, butanol, acetone, and the like. If so desired, the organic solvents may be additionally controllably acidified with an inorganic or organic acid. If so desired, the pH of the organic solvents may be additionally controllably manipulated with an inorganic or organic base. The vessel 40 is controllably pressurized and temperature controlled to enable manipulation of pressure and temperature so that target cooking conditions are provided while the solvent is commingling with the feedstock. Exemplary cooking conditions include pressures in the range of about 15-40 bar (g), temperatures in the range of about 120-350° C., and pHs in the range of about 0.5-5.5. During the cooking process, lignins and lignin-containing compounds contained within the commingled and impregnated lignocellulosic feedstock will be dissolved into the organic solvent resulting in the cellulosic fibrous materials previously adhered thereto and therewith to disassociate and to separate from each other. Those skilled in these arts will understand that in addition to the dissolution of lignins and lignin-containing polymers, the cooking process will release monosaccharides, oligosaccharides and polysaccharides and other organic compounds for example acetic acid, furfural, 5-hydroxymethyl furfural (5-HMF), other organic acids such as formic and levulinic acids in solute and particulate forms, from the lignocellulosic materials into the organic solvents. Those skilled in these arts refer to such organic solvents containing the lignins, lignin-containing compounds, monosaccharides, oligosaccharides, polysaccharides, hemicelluloses and other organic compounds extracted from the lignocellulosic feedstock, as "black liquors" or "spent liquors". The disassociated cellulosic fibrous materials released from the feedstock are conveyed to the second end of the vessel 40 where they are discharged via a second auger feeder 50 which compresses the cellulosic fibrous materials into a solids fraction, i.e., a pulp which is then conveyed to the second module B. The black liquors are discharged as a liquid fraction from about the first end of the digestion/extraction vessel 40 into a pipeline 47 for conveyance to the third module C.

The second module B is provided with a mixing vessel 60 wherein the viscosity of solids fraction, i.e., pulp discharged from the first module A is controllably reduced to a selected target viscosity, by commingling with a recovered recycled solvent stream delivered by a pipeline 130 from a downstream component of module B. The reduced viscosity pulp is then transferred to a digestion vessel 70 where a suitable enzymatic preparation is intermixed and commingled with the pulp for progressively breaking down the cellulosic fibers, suspended solids and dissolved solids into hemicelluoses, other polysaccharides, oligosaccharides and monosaccharides. A liquid stream comprising these digestion products is transferred from the digestion vessel 70 to a fermentation vessel 80 and is commingled with a suitable microbial inoculum selected for fermentation of hexose and pentose monosaccharides and/or oligosaccharides in the liquid stream thereby producing a fermentation beer comprising at least a short-chain alcohol exemplified by ethanol, residual sediments and lees. The fermentation beer is transferred to a first distillation tower 90 for refining by volatilizing then distilling and separately collecting from the top of the distillation tower 90 an ethanol stream which is transferred and stored in a suitable holding container 100. The ethanol stream may be further refined, for example by distillation, into one or more of a fuel-grade ethanol stream, an industrial-grade ethanol stream, and a potable ethanol stream. The remaining liquid stillage is optionally removed from the bottom of distillation tower 90 to equipment 110 configured to precipitate and separate VHMW lignins which are then collected and stored in a suitable vessel 120 for further processing and/or shipment. It is within the scope of the present invention to heat the stillage and flash it with cold water to facilitate precipitation of the VHMW lignins. The detoxified stillage may then be controllably recycled from equipment 110 via pipeline 130 to the mixing vessel 60 for reducing the viscosity of fresh incoming pulp from the first module A. However, the remaining liquid stillage may be optionally recovered if so desired, for alternative processing and/or disposal without first separating and recovering therefrom the plurality of VHMW lignin derivatives.

Suitable enzyme preparations for addition to digestion vessel 70 for progressively breaking down cellulosic fibers into hemicelluloses, polysaccharides, oligosaccharides and monosaccharides may comprise one or more of enzymes exemplified by endo-β-1,4-glucanases, cellobiohydrolases, β-glucosidases, β-xylosidases, xylanases, α-amylases, β-amylases, pullulases, esterases, other hemicellulases and cellulases and the like.

Suitable microbial inocula for fermenting pentose and/or hexose monosaccharides in fermentation vessel 80 may comprise one or more suitable strains selected from yeast species, fungal species and bacterial species. Suitable yeasts are exemplified by *Saccharomyces* spp. and *Pichia* spp. Suitable *Saccharomyces* spp are exemplified by *S. cerevisiae* such as strains Sc Y-1528, Tembec-1 and the like. Suitable fungal species are exemplified by *Aspergillus* spp. and *Trichoderma* spp. Suitable bacteria are exemplified by *Escherichia coli, Zymomonas* spp., *Clostridium* spp., and *Corynebacterium* spp. among others, naturally occurring and genetically modified. It is within the scope of the present invention to provide an inoculum comprising a single strain, or alternatively a plurality of strains from a single type of organism, or further alternatively, mixtures of strains comprising strains from multiple species and microbial types (i.e. yeasts, fungi and bacteria).

The black liquors discharged as a liquid fraction from the digestion/extraction vessel 40 of third module A, are processed in module C to recover at least a portion of the digestion/extraction solvent comprising the black liquors, and to separate useful components extracted from the lignocellulosic feedstocks as will be described in more detail below. The HMW lignin derivatives have a tendency to self-precipitate from the black liquor liquid stream as it cools upon egress from the first module A, and therefore may be separated from the black liquor liquid stream by a suitable solids-liquids separation equipment 150 as exemplified by filtering apparatus, hydrocyclone separators, centrifuges and other such equipment known to those skilled in these arts. It is suitable to provide cooling to the black liquor liquid egress lines to facilitate the self-precipation of the HMW lignins. The partially de-lignified black liquor liquid stream egressing from the solids-liquids separation equipment 150 is transferred into a heating tower 140 wherein it is first heated then transferred to mixing tank 160 wherein it is rapidly mixed (i.e., "flashed") and commingled with a supply of cold water thereby precipitating MMW lignins from the partially de-lignified black liquor. The precipitated MMW lignins are separated from the water-diluted black liquor liquid stream by a suitable solids-liquids separation equipment 165 as exemplified by filtering apparatus, hydrocyclone separators, centrifuges and other such equipment. The separated MMW lignins are transferred to a lignin drier 165 for controlled removal of excess moisture, after which the dried MMW lignins are transferred to a storage bin 170 for packaging and shipping. The de-lignified filtrate egressing from the solids-liquids separation equipment 165 is transferred to a second distillation tower 180 for vaporizing, distilling and recovering therefrom at least a portion of the organic solvents used for fractionating the lignocellulosic feedstocks, remaining therein. In the case where short-chain alcohols exemplified by ethanol are used for fractionating the lignocellulosic feedstocks, the recovered organic solvent will comprise ethanol, and is transferred to a digestion/extraction solvent holding tank 250 where it may, if so desired, be commingled with a portion of ethanol produced in module B and drawn from pipeline 95, to controllably adjust the concentration and composition of the digestion/extraction solvent prior to supplying the digestion/extraction solvent via pipeline 41 to the digestion/extraction vessel 40 of module A. It is within the scope of the present invention to recover furfurals from the de-lignified filtrate fraction concurrent with the vaporization and distillation processes within the second distillation tower, and to transfer the recovered furfurals to a storage tank 190. An exemplary suitable process for recovering furfurals is to acidify the heated de-lignified filtrate thereby condensing furfurals therefrom. It is within the scope of the present invention to supply suitable liquid bases or acids to controllably adjust the pH of the de-lignified filtrate fraction. Suitable liquid bases are exemplified by sodium hydroxide. Suitable acids are exemplified by sulfuric acid.

The stillage from the second distillation tower 180 is transferred to the fourth module D for further processing and separation of useful products therefrom. The hot stillage may be transferred into a cooling tower 200 configured to collect a condensate comprising acetic acid which is then transferred to a suitable holding vessel 210. The de-acidified stillage may then transferred to a stillage processing vessel 220 configured for heating the stillage followed by flashing with cold water thereby precipitating VLMW lignins which are then separated from a sugar syrup stream, and a semi-solid/solid waste material discharged into a waste disposal bin 226. The VLMW lignins are transferred to a suitable holding container 230 for further processing and/or shipment. The sugar syrup stream, typically comprising at least one of xylose, arabinose, glucose, mannose and galactose, is passed through a decanter 240 which separates VLMW lignins from the sugar syrup stream thereby purifying the sugar syrup stream which is transferred to a suitable holding tank 247 prior to further processing and/or shipping, The VLMW lignins are transferred to a suitable holding tank 245 prior to further processing and/or shipping. It is within the scope of the present invention to divert from the fourth module D some or all of the stillage recovered from the second distillation tower 180 in the third module C, for suitable disposal thereof or alternatively, for processing by anaerobic digestion.

Figure 3:
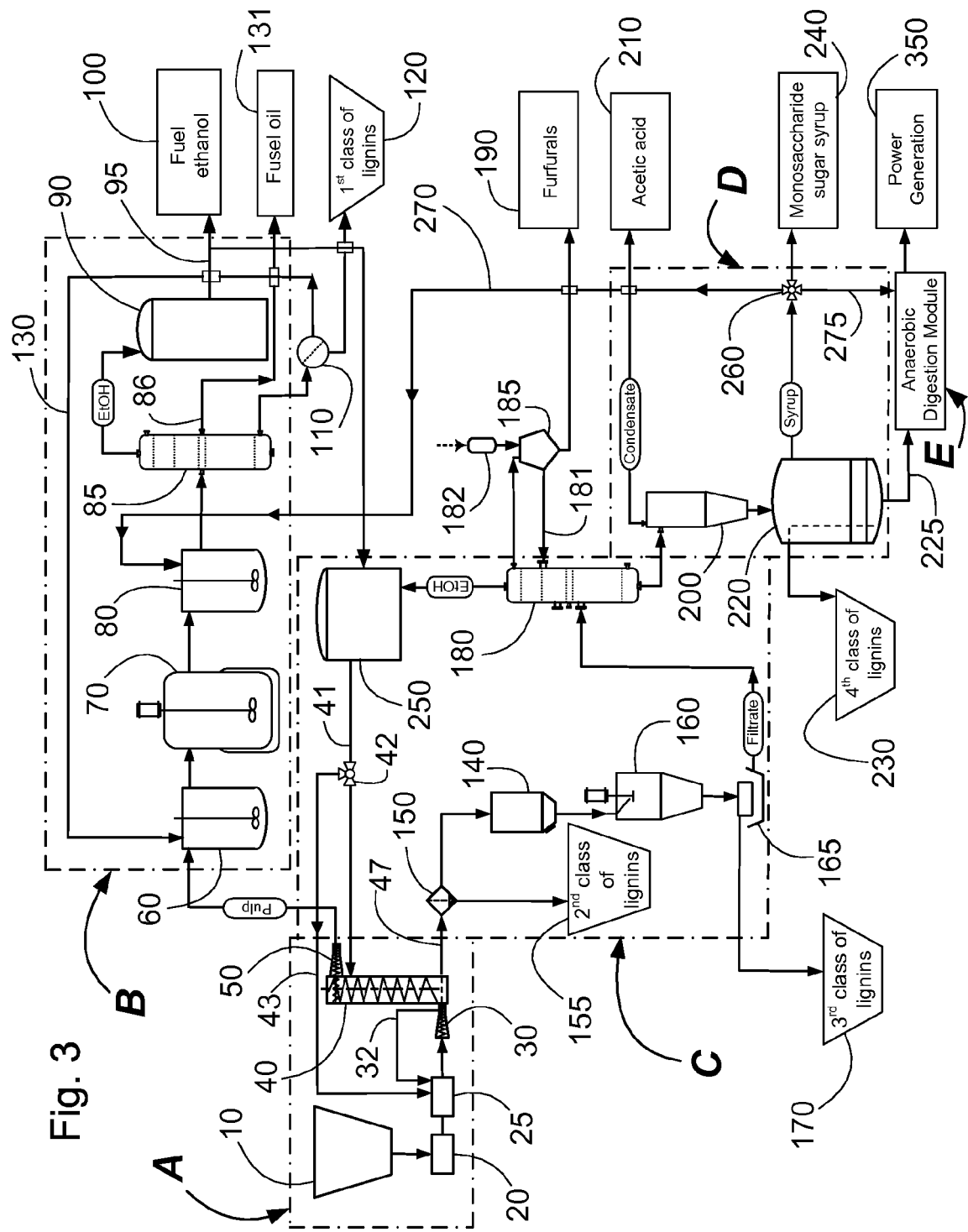
FIG. 3 is a schematic flowchart of the system from FIG. 2 additionally provided with a device for optionally diverting the sugar output stream to (a) the fuel ethanol production module, and (b) an anaerobic digestion module.

FIG. 3 illustrates exemplary modifications that are suitable for the modular lignocellulosic feedstock processing system of the present invention.

One exemplary embodiment includes provision of a pretreatment vessel 25 for receiving therein processed lignocellulosic feedstock from the separating device 20 for pre-treatment prior to digestion and extraction by commingling and saturation with a heated digestion/extraction solvent for a suitable period of time. A suitable supply of digestion/extraction solvent may be diverted from pipeline 41 by a valve 42 and delivered to the pre-treatment vessel 25 by pipeline 43. Excess digestion/extraction solvent is squeezed from the processed and pre-treated lignocellulosic feedstock by the mechanical pressures applied by the first auger feeder 30 during transfer of the feedstock into the digestion/extraction vessel 40. The extracted digestion/extraction solvent is recyclable via pipeline 32 back to the pre-treatment vessel 25 for commingling with incoming processed lignocellulosic feedstock and fresh incoming digestion/extraction solvent delivered by pipeline 43. Such pre-treatment of the processed lignocellulosic feedstock prior to its delivery to the digestion/extraction vessel 40 will facilitate the rapid absorption of digestion/extraction solvent during the commingling and cooking process and expedite the digestion of the lignocellulosic feedstock and extraction of components therefrom.

Another exemplary embodiment illustrated in FIG. 2 provides a second diverter valve 260 interposed the sugar syrup stream discharged from the decanter 240 in module D. In addition to directing the sugar stream to the sugar stream holding tank 240, the second diverter valve 260 is configured for controllably diverting a portion of the liquid sugar stream into a pipeline 270 for delivery into the fermentation tank 80 in module B. Such delivery of a portion of the liquid sugar stream from module D will enhance and increase the rate of fermentation in tank 80 and furthermore, will increase the volume of ethanol produced from the lignocellulosic feedstock delivered to module A.

Figure 4:
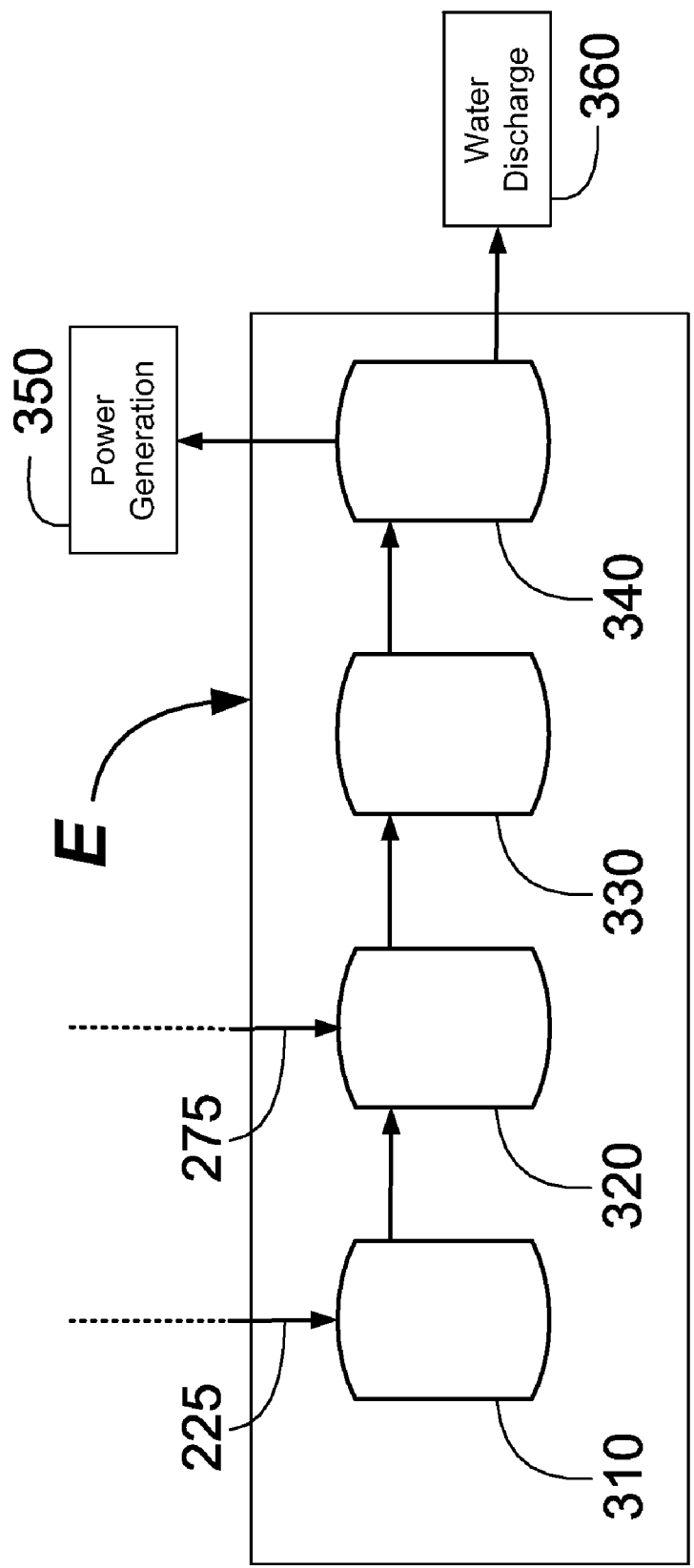
FIG. 4 is a schematic flowchart of an exemplary anaerobic digestion module suitable for cooperating with the modular continuous counter-flow system of the present invention for processing a lignocellulosic feedstock.

Another exemplary embodiment illustrated in FIG. 2 provides an optional fifth module E comprising an anaerobic digestion system configured to receive semi-solid/solid wastes from the stillage processing vessel 220 and optionally configured for receiving a portion of the sugar syrup stream discharged from the stillage processing vessel 220. An exemplary anaerobic digestion system comprising module E of the present invention is illustrated in FIG. 4 and generally comprises a sludge tank 310, a vessel 320 configured for containing therein biological acidification processes (referred to hereinafter as an acidification vessel), a vessel 330 configured for containing therein biological acetogenesis processes (referred to hereinafter as an acetogenesis vessel), and a vessel 340 configured for containing therein biological processes for conversion of acetic acid into biogas (referred to hereinafter as a biogas vessel). The semi-solid/solid waste materials produced in the stillage processing vessel 220 of module C are transferred by a conveyance apparatus 225 to the sludge tank 310 wherein anaerobic conditions and suitable populations of facultative anaerobic microorganisms are maintained. Enzymes produced by the facultative microorganisms hydrolyze the complex organic molecules comprising the semi-solid/solid waste materials into soluble monomers such as monosaccharides, amino acids and fatty acids. It is within the scope of the present invention to provide if so desired inocula compositions for intermixing and commingling with the semi-solid/solid wastes in the sludge tank 310 to expedite the hydrolysis processes occurring therein. Suitable hydrolyzing inocula compositions are provided with at least one *Enterobacter* sp. A liquid stream containing therein the hydrolyzed soluble monomers is transferred into the acidification vessel 320 wherein anaerobic conditions and a population of acidogenic bacteria are maintained. The monosaccharides, amino acids and fatty acids contained in the liquid stream received by the acidification vessel 320 are converted into volatile acids by the acidogenic bacteria. It is within the scope of the present invention to provide if so desired acidification inocula compositions configured for facilitating and expediting the production of solubilized volatile fatty acids in the acidification tank 320. Suitable acidification inocula compositions are provided with at least one of *Bacillus* sp., *Lactobacillus* sp. and *Streptococcus* sp. A liquid stream containing therein the solubilized volatile fatty acids is transferred into the acetogenesis vessel 330 wherein anaerobic conditions and a population of acetogenic bacteria are maintained. The volatile fatty acids are converted by the acetogenic bacteria into acetic acid, carbon dioxide, and hydrogen. It is within the scope of the present invention to provide if so desired inocula compositions configured for facilitating and expediting the production of acetic acid from the volatile fatty acids delivered in the liquid stream into in the acetogenesis vessel 330. Suitable acetification inocula compositions are provided with at least one of *Acetobacter* sp., *Gluconobacter* sp., and *Clostridium* sp. The acetic acid, carbon dioxide, and hydrogen are then transferred from the acetogenesis vessel 330 into the biogas vessel 340 wherein the acetic acid is converted into methane, carbon dioxide and water. The composition of the biogas produced in the biogas vessel 330 of module E will vary somewhat with the chemical composition of the lignocellulosic feedstock delivered to module A, but will typically comprise primarily methane and secondarily $CO_2$, and trace amounts of nitrogen gas, hydrogen, oxygen and hydrogen sulfide. It is within the scope of the present invention to provide if so desired methanogenic inocula compositions configured for facilitating and expediting the conversion of acetic acid to biogas. Suitable methanogenic inocula compositions are provided with at least one of bacteria are from the *Methanobacteria* sp., *Methanococci* sp., and *Methanopyri* sp. The biogas can be fed directly into a power generation system as exemplified by a gas-fired combustion turbine. Combustion of biogas converts the energy stored in the bonds of the molecules of the methane contained in the biogas into mechanical energy as it spins a turbine. The mechanical energy produced by biogas combustion, for example, in an engine or micro-turbine may spin a turbine that produces a stream of electrons or electricity. In addition, waste heat from these engines can provide heating for the facility's infrastructure and/or for steam and/or for hot water for use as desired in the other modules of the present invention.

However, a problem with anaerobic digestion of semi-solid/solid waste materials is that the first step in the process, i.e., the hydrolysis of complex organic molecules comprising the semi-solid/solid waste materials into a liquid stream containing soluble monomers such as monosaccharides, amino acids and fatty acids, is typically lengthy and variable, while the subsequent steps, i.e., acidification, acetification, and biogas production proceed relatively quickly in comparison to the first step. Consequently, such lengthy and variable hydrolysis in the first step of anaerobic may result in insufficient amounts of biogas production relative to the facility's requirements for power production and/or steam and/or hot water. Accordingly, another embodiment of the present invention, as illustrated in FIGS. 3 and 4, controllably provides a portion of the sugar syrup stream discharged from the stillage processing vessel 220 of module D, to the acidification tank 320 of module E to supplement the supply of soluble monosaccharides and/or oligosaccharides hydrolyzed from semi-solid/solid materials delivered to the sludge tank 310. Thus, the amount of biogas produced by module E of the present invention can be precisely manipulated and modulated by providing a second diverter 260 interposed the sugar syrup discharge line from stillage processing vessel 220, to controllably divert a portion of the sugar syrup into pipeline 275 for transfer to the acidification vessel 320.

Figure 5:
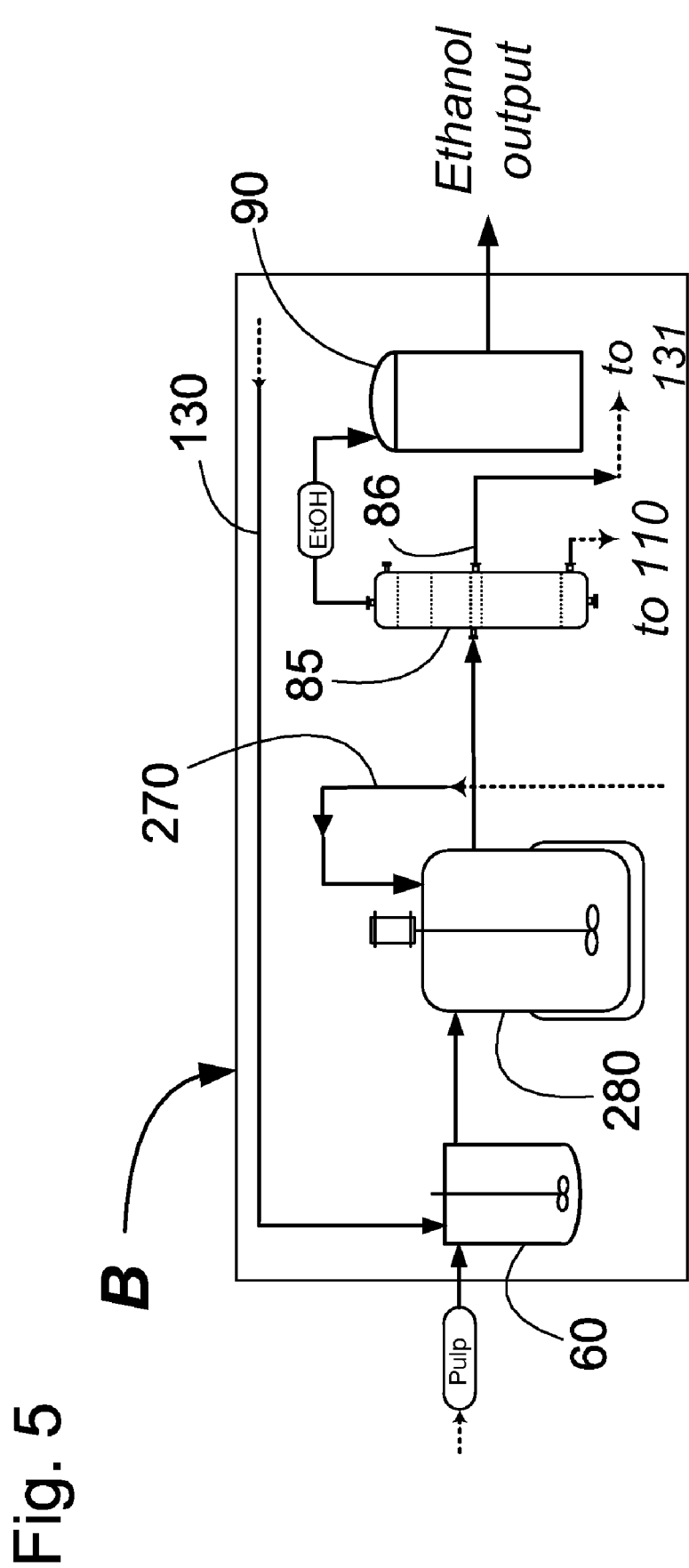
FIG. 5 is schematic flowchart showing an alternative configuration of the fuel ethanol production module for concurrent saccharification and fermentation processes within a single vessel.

Another exemplary embodiment of the present invention is illustrated in FIG. 5 and provides an optional vessel 280 for module B, wherein vessel 280 is configured for receiving the reduced viscosity pulp from mixing vessel 60 (FIGS. 2, 3) and for concurrent i.e., co-saccharification and co-fermentation therein of the reduced-viscosity solids fractions. Those skilled in these arts will understand that such co-saccharification and co-fermentation processes are commonly referred to as "simultaneous saccharification and fermentation" (SSF) processes, and that vessel 280 (referred to hereinafter as a SSF vessel) can replace digestion vessel 70 and fermentation vessel 80 shown in FIGS. 2 and 3. It is suitable to provide a supplementary stream of sugar syrup into the SSF vessel 280 via pipeline 270 from the second diverter valve 260 (FIGS. 2 and 5) to controllably enhance and increase the rate of fermentation in the SSF vessel 280.

Figure 6:
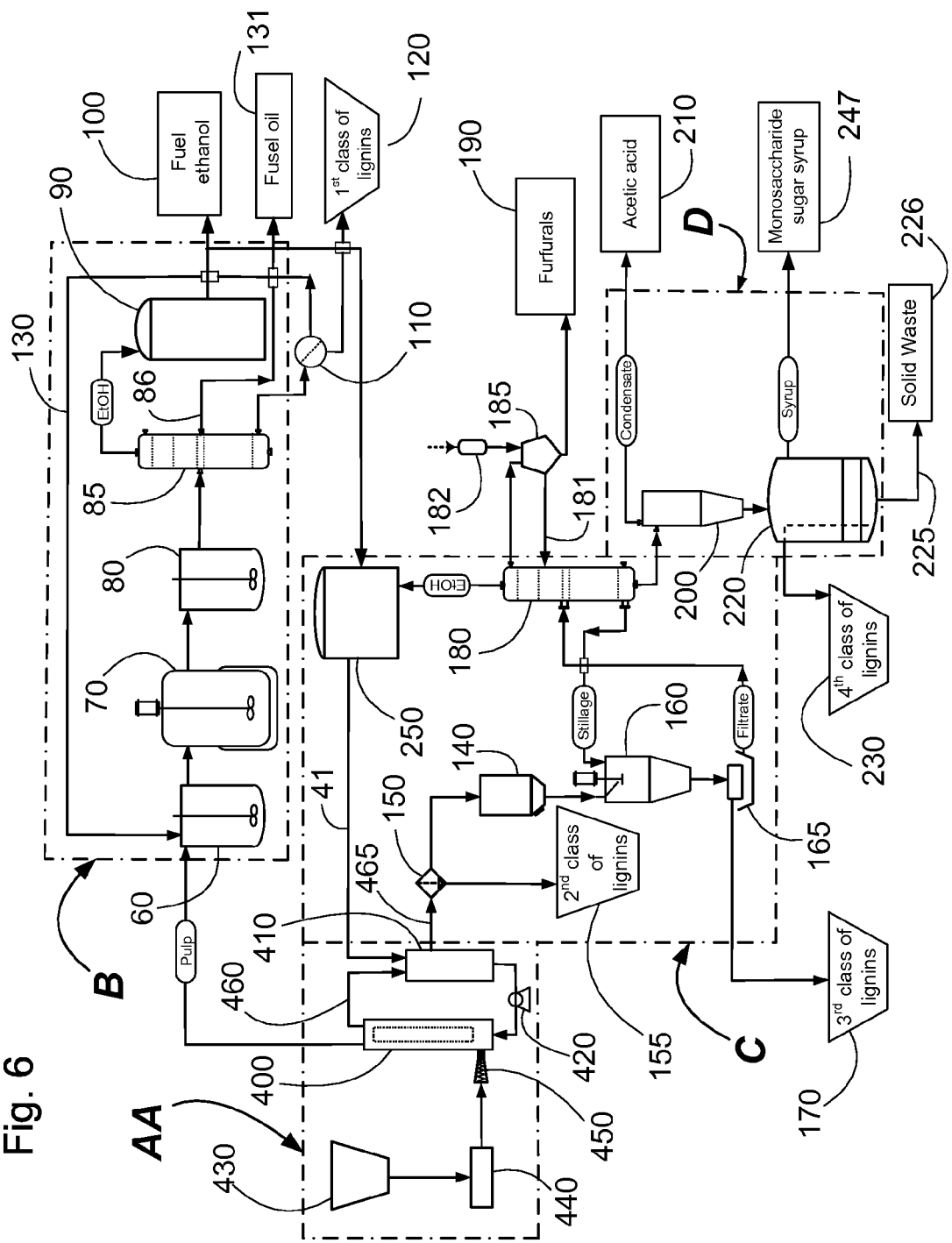
FIG. 6 is a schematic flowchart of a continuous counter-flow processing system of the process re-configured into a batch through-put system.

Another exemplary embodiment of the present invention is illustrated in FIG. 6 and provides an alternative first module AA, for communication and cooperation with modules B and C, wherein the alternative first module AA (FIG. 6) is configured for receiving, processing and digestion/extraction of batches of a lignocellulosic feedstock, as compared to module A which is configured for continuous inflow, processing and digestion/extraction of a lignocellulosic feedstock (FIG. 2). As shown in FIG. 6, one exemplary embodiment for batch digestion/extraction of a lignocellulosic feedstock comprises a batch digestion/extraction vessel 400 interconnected and communicating with a digestion/extraction solvent re-circulating tank 410 and a solvent pump 420. A batch of lignocellulosic feedstock is loaded into a receiving bin 430 from where it is controllably discharged into a conveyance system provided with a screening device 440 configured for removing pebbles, gravel, metals and other debris. The screening device 440 may be optionally configured for sizing the lignocellulosic feedstock into desired fractions. The processed lignocellulosic feedstock is then conveyed with a third auger feeder 450 into a first end of the batch digestion/extraction vessel 400. The digestion/extraction solvent re-circulating tank 410 is configured to receive a suitable digestion/extraction solvent from the digestion/extraction solvent holding tank 250 of module B via pipeline 41. The digestion/extraction solvent is pumped via solvent pump 420 into the batch digestion/extraction vessel 400 wherein it controllably commingled, intermixed and circulated through the batch of lignocellulosic feedstock contained therein. The batch digestion/extraction vessel 400 is controllably pressurized and temperature controlled to enable manipulation of pressure and temperature so that target cooking conditions are provided while the solvent is commingling and intermixing with the feedstock. Exemplary cooking conditions include pressures in the range of about 15-30 bar(g), temperatures in the range of about 120°-350° C., and pHs in the range of about 1.5-5.5. During the cooking process, lignins and lignin-containing compounds contained within the commingled and impregnated lignocellulosic feedstock will be dissolved into the organic solvent resulting in the cellulosic fibrous materials adhered thereto and therewith to disassociate and to separate from each other. Those skilled in these arts will understand that in addition to the dissolution of lignins and lignin-containing polymers, the cooking process will release monosaccharides, oligosaccharides and polysaccharides and other organic compounds for example acetic acid, in solute and particulate forms, from the lignocellulosic materials into the organic solvents. It is suitable to discharge the digestion/extraction solvent from the batch digestion/extraction vessel 400 through pipeline 460 during the cooking process for transfer via pipeline 460 back to the digestion/extraction solvent re-circulating tank 410 for re-circulation by the solvent pump 420 back into the batch digestion/extraction vessel 400 until the lignocellulosic feedstock is suitable digested and extracted into a solids fraction comprising a viscous pulp material comprising dissociated cellulosic fibers, and a liquids fraction, i.e., black liquor, comprising solubilized lignins and lignin-containing polymers, hemicelluloses, other polysaccharides, oligosaccharides, monosaccharides and other organic compounds in solute and particulate forms, from the lignocellulosic materials in the spent organic solvents. It is within the scope of the present invention to withdraw a portion of the re-circulating digestion/extraction solvent from the solvent re-circulating tank 410 via pipeline 465 for transfer to the heating tower 140 in module C, and to replace the withdrawn portion of re-circulating digestion/extraction solvent with fresh digestion/extraction solvent from the digestion/extraction solvent holding tank 250 of module B via pipeline 41, thereby expediting the digestion/extraction processes within the batch digestion/extraction vessel 400. After digestion/extraction of the lignocellulosic feedstock has been completed, the solids fraction comprising cellulosic fibre pulp is discharged from the batch digestion/extraction vessel 400 and conveyed to the mixing vessel 60 in module B wherein the viscosity of the solids fraction, i.e., pulp discharged from the first module AA, is controllably reduced to a selected target viscosity by commingling and intermixing with de-lignified stillage delivered via pipeline 130 then be controllably recycled from de-lignification equipment 110 of module B after which the reduced-viscosity pulp is further processed by saccharification, fermentation and refining as previously described. The black liquor is transferred from the digestion/extraction solvent re-circulating tank 410 via pipeline 465 to the heating tower 140 in module C for precipitating lignin therefrom and further processing as previously described.

Figure 7:
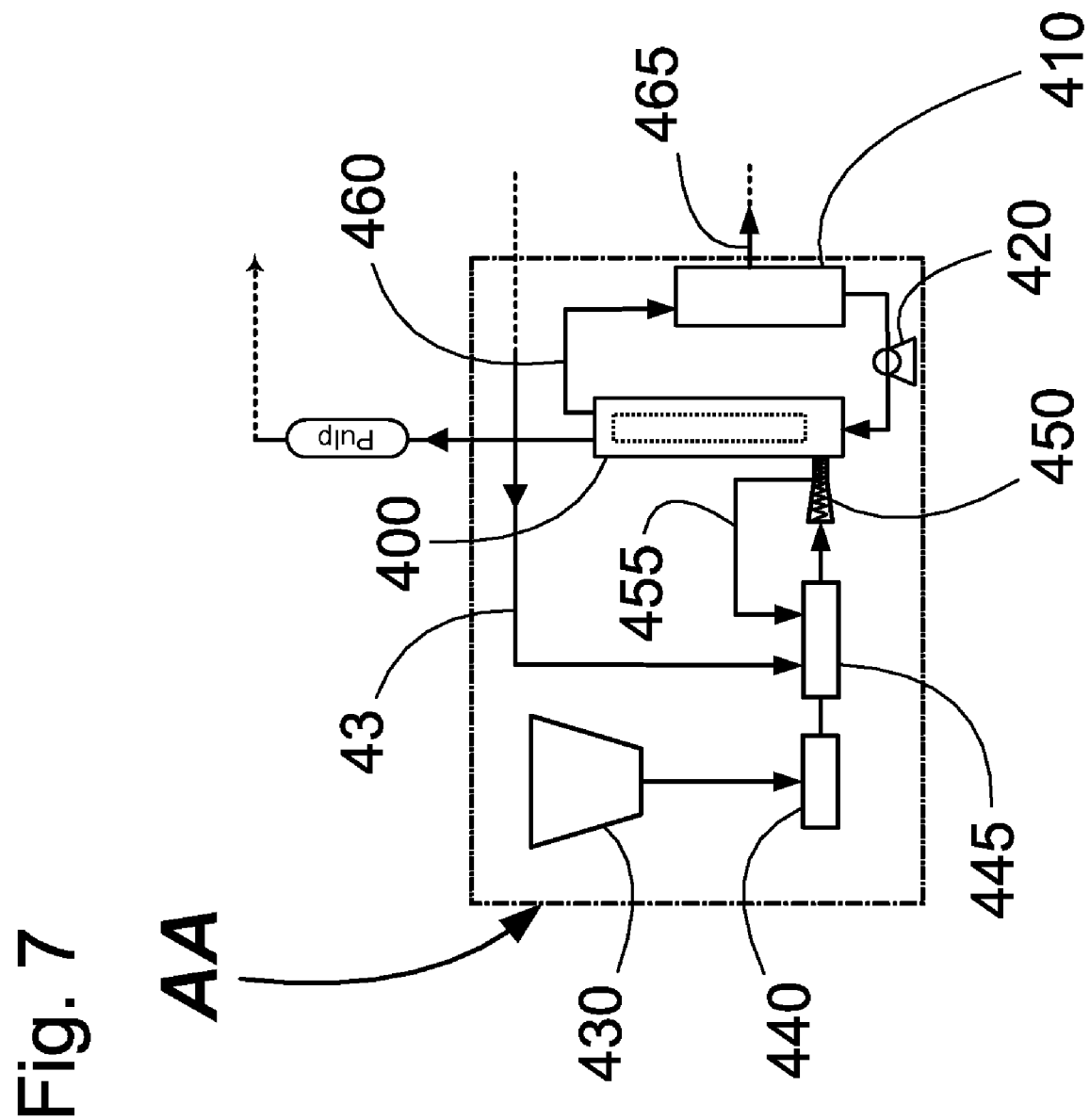
FIG. 7 is a schematic flowchart showing an alternative configuration for the batch throughput system shown in FIG. 6.

A suitable exemplary modification of the batch digestion/extraction module component of the present invention is illustrated in FIG. 7, wherein a pre-treatment vessel 445 is provided for receiving therein processed lignocellulosic feedstock from the screening device 440 for pre-treatment prior to conveyance to the batch digestion/extraction vessel 400, by commingling and saturation with a digestion/extraction solvent for a suitable period of time. A suitable supply of digestion/extraction solvent may be diverted from pipeline 41 by a valve 42 (shown in FIG. 3) and delivered to the pre-treatment vessel 445 by pipeline 43. Excess digestion/extraction solvent is squeezed from the processed and pre-treated lignocellulosic feedstock by the mechanical pressures applied by the third auger feeder 450 during transfer of the feedstock into the batch digestion/extraction vessel 400. The extracted digestion/extraction solvent is recyclable via pipeline 455 back to the pre-treatment vessel 445 for commingling with incoming processed lignocellulosic feedstock and fresh incoming digestion/extraction solvent delivered by pipeline 43. Such pre-treatment of the processed lignocellulosic feedstock prior to its delivery to the batch digestion/extraction vessel 400 will facilitate the rapid absorption of digestion/extraction solvent during the commingling and cooking process and expedite the digestion of the lignocellulosic feedstock and extraction of components therefrom.

Another exemplary embodiment of the present invention relates to processes, systems and equipment configured for de-lignifying from the cellulosic solids stream recovered from the first module A, the plurality of VHMW lignin derivatives that are integrally but incidentally associated therewith the cellulosic solids stream after fractionation of the lignocellulosic feedstocks with one or more organic solvents has been completed in the first module A, and the cellulosic solids stream has been separated from the black liquor liquid stream. According to one aspect, the second module B may be optionally configured to receive and delignify the cellulosic solids stream separated from the first module A, by bleaching the pulp with an adaptation of one of an elemental chlorine-free (ECF) process or a total chlorine-free (TCF) process. An exemplary suitable ECF process comprises washing the cellulosic solids stream with 3%-4% chlorine dioxide at a temperature selected from the range of about 60° C. to about 80° C., followed by a wash with a dilute alkali solution at a temperature selected from the range of about 45° C. to about 90° C., followed by a second wash with 3-4% chlorine dioxide at a temperature selected from the range of about 60° C. to about 80° C. thereby producing a de-lignified cellulose pulp which is washed several times with warm water. It is optional to wash the pulp with warm water between each of the de-lignification washes. It is also optional to commingle ozone with chlorine dioxide in one of the de-lignifying washing step. It is also optional to perform the dilute alkali wash inside a vessel pressurized with oxygen. An exemplary suitable TCF process comprises washing the cellulosic solids stream with a mild alkali solution at a temperature ranging from about 60° C. to about 80° C. in a vessel pressurized with oxygen, followed by at least two washes with hydrogen peroxide, thereby producing a de-lignified cellulose pulp. It is optional to wash the cellulose pulp with warm water between each of the de-lignification washes. The de-lignified cellulose pulp may be recovered from the second module B for further processing to configure cellulose-comprising compositions. In this exemplary embodiment, the second module B may be additionally configured for collecting the spent de-lignification washings and water washing, and recovering at least a portion of the plurality of VHMW lignin derivatives de-lignified from the cellulosic solids stream.

Another exemplary embodiment of the present invention relates to additional processes, systems and equipment configurations provided in the second module B configured for de-lignifying the cellulosic solids stream recovered from the first module A, wherein the de-lignified cellulose pulp is controllably separated by enzymatic hydrolysis into a carbohydrates stream comprising at least monosaccharides. Suitable enzymes are exemplified by endo-β-1,4-glucanases, cellobiohydrolases, β-glucosidases, cellulases, and the like. The carbohydrates stream may be recovered from the second module B as a final product stream. Alternatively, the carbohydrates stream may be fermented in a suitable fermentation vessel to produce a short-chain alcohol stream exemplified by butanol and ethanol. The short-chain alcohol stream may be furthered refined, for example by distillation, into one or more of a fuel-grade short-chain alcohol stream, an industrial-grade short-chain alcohol stream, and if the short-chain alcohol stream is an ethanol stream, into a potable ethanol stream. Suitable microbial inocula for fermenting such carbohydrate streams may comprise one or more suitable strains selected from yeast species, fungal species and bacterial species. Suitable yeasts are exemplified by *Saccharomyces* spp. and *Pichia* spp. Suitable *Saccharomyces* spp are exemplified by *S. cerevisiae* such as strains Sc Y-1528, Tembec-1 and the like. Suitable fungal species are exemplified by *Aspergillus* spp. and *Trichoderma* spp. Suitable bacteria are exemplified by *Escherichia coli*, *Zymomonas* spp., *Clostridium* spp., and *Corynebacterium* spp. among others, naturally occurring and genetically modified. It is within the scope of the present invention to provide an inoculum comprising a single strain, or alternatively a plurality of strains from a single type of organism, or further alternatively, mixtures of strains comprising strains from multiple species and microbial types (i.e. yeasts, fungi and bacteria).

Those skilled in these arts will understand that cellulose is a polymer of β-D-glucose units that are linked together by 1-4 glycosidic bonds to form cellobiose residues that are the repeating units in cellulose fibrils which in turn, are intertwined to form cellulose fibers. Cellulose consists of ordered crystalline regions wherein the adjacent glycans are held together by hydrogen bonds randomly interspaced by disordered amorphous regions of adjacent glycans. It is known that amorphous regions of cellulose are more predisposed to hydrolysis by cellulytic enzyme activity, than are the crystalline regions. Accordingly, another exemplary embodiment of the present invention relates to optional methods and systems design for decrystallization of the cellulosic stream in the second module B prior to enzymatic hydrolysis. The decrystallation step may be provided after, or alternatively, before adjustment of the viscosity of the cellulosic solids stream received from the first module A. The decrystallation step may be provided after the cellulosic solids stream has been de-lignified. The cellulosic solids stream or alternatively, the de-lignified cellulosic pulp stream, may be decrystallized by commingling the stream with a suitable decrystallation treatment and then washing well the decrystallized stream with water before commencing with enzymatic hydrolysis. Suitable decrystallization treatments are exemplified among others by phosphoric acid, trifloroacetic acid, monoethylamine, sodium hydroxide, ionic liquids comprising one or more of methylimidazolium ions, pyridinium ions, pyrrolidinium ions, phosphonium ions, ammonium ions among others, and suitable combinations thereof.

Figure 8:
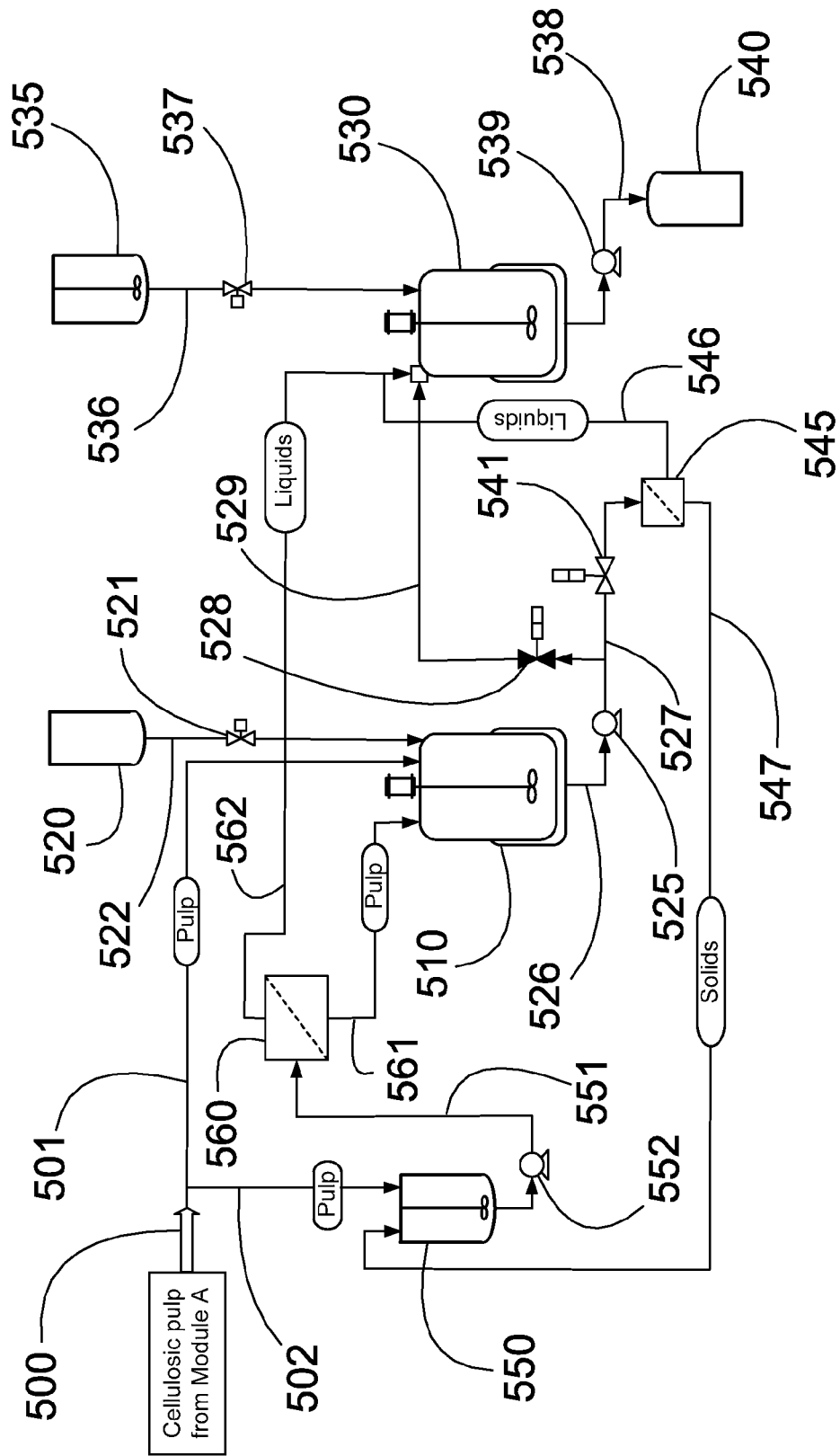
FIG. 8 is a schematic flowchart showing an exemplary optional systems design for a hybrid saccharification and fermentation module generally configured for receiving and processing therein a cellulosic solids stream according to an exemplary embodiment of the modular biorefinery of the present invention, wherein the optional systems design is configured for recovery and recycling of hydrolytic enzymes from a saccharification tank.

Another exemplary embodiment of the present invention relates to processes, systems and equipment configured for recovery and recycling of hydrolytic enzymes provided in the second module B for separation of cellulose pulps into one or more of monosaccharides, polysaccharides and oligosaccharides. According to one aspect, the hydrolytic enzymes are recovered after saccharification during transfer of a monosaccharides stream to a fermentation tank for conversion to a short-chain alcohol. An illustrative schematic flowchart generally outlining an enzyme recovery and recycling system loop cooperating with a hybrid saccharification and fermentation (HSF) system is shown in FIG. 8 wherein a cellulosic pulp stream 500 recovered from a first module A, is delivered to a saccharification tank 510 via a suitable pipeline 501. A suitable preparation comprising fresh hydrolytic enzymes is delivered to the saccharification tank 510 via line 522 from an enzyme holding tank 520. The delivery of the enzyme preparation to the saccharification tank 510 is controllable by valve 521 interposed line 522. After a suitable time period of saccharification under suitable physical conditions (i.e., temperature and pressure), the hydrolysate comprising a solubilized carbohydrates stream and digested solids are removed from saccharification tank 510 via outlet line 526 with the aid of a pump 526 and are transferred to a fermentation tank 530. Those skilled in these arts will understand that a large portion of the hydrolytic enzymes added to saccharification tank 510 will be attached to the spent solids and the remainder will be distributed throughout the solubilized carbohydrates stream. The flow of the hydrolysate and digested solids from the saccharification tank 510 to the fermentation tank 530 is controllable and manipulable by diverter valves 528, 541. A portion of the flow of the hydrolysate and digested solids may be optionally diverted to a solid/liquid separation unit 545 wherefrom the liquids are transferred via line 546 to the fermentation tank 530 wherein they are commingled with the liquid carbohydrates hydrolysate stream delivered by line 529. The settled solids are transferred via line 547 to an enzyme recovery tank 550 where the settled solids with enzymes attached thereto are reconditioned by commingling and intermixing with fresh cellulosic pulp stream 500 via pipeline 502. The reconditioned enzyme solids stream is transferred via pipeline 551 by pump 552 to a solid/liquid separation tank 560 from where the reconditioned enzymes are transferred via pipeline 561 back to the saccharification tank 510 for hydrolysis of fresh cellulosic pulp stream 500 via pipeline 501, while the separated liquids are transferred to the fermentation tank 530 via pipeline 562. Additional fresh enzymes may be controllably added, if so desired, to the saccharification tank 510 from the fresh enzyme holding tank 520 via line 522. A suitable inoculum comprising fermentative microorganism is controllably delivered to the fermentation tank 530 via line 536 and valve 437 from a holding tank 535. The fermentation beer comprising short-chain alcohols and spent solids is transferred from the fermentation tank 530 via line 538 by pumping with pump 539 to a fermentation beer holding tank 540, from where it is transferred for further processing and refining as described elsewhere herein.

Figure 9:
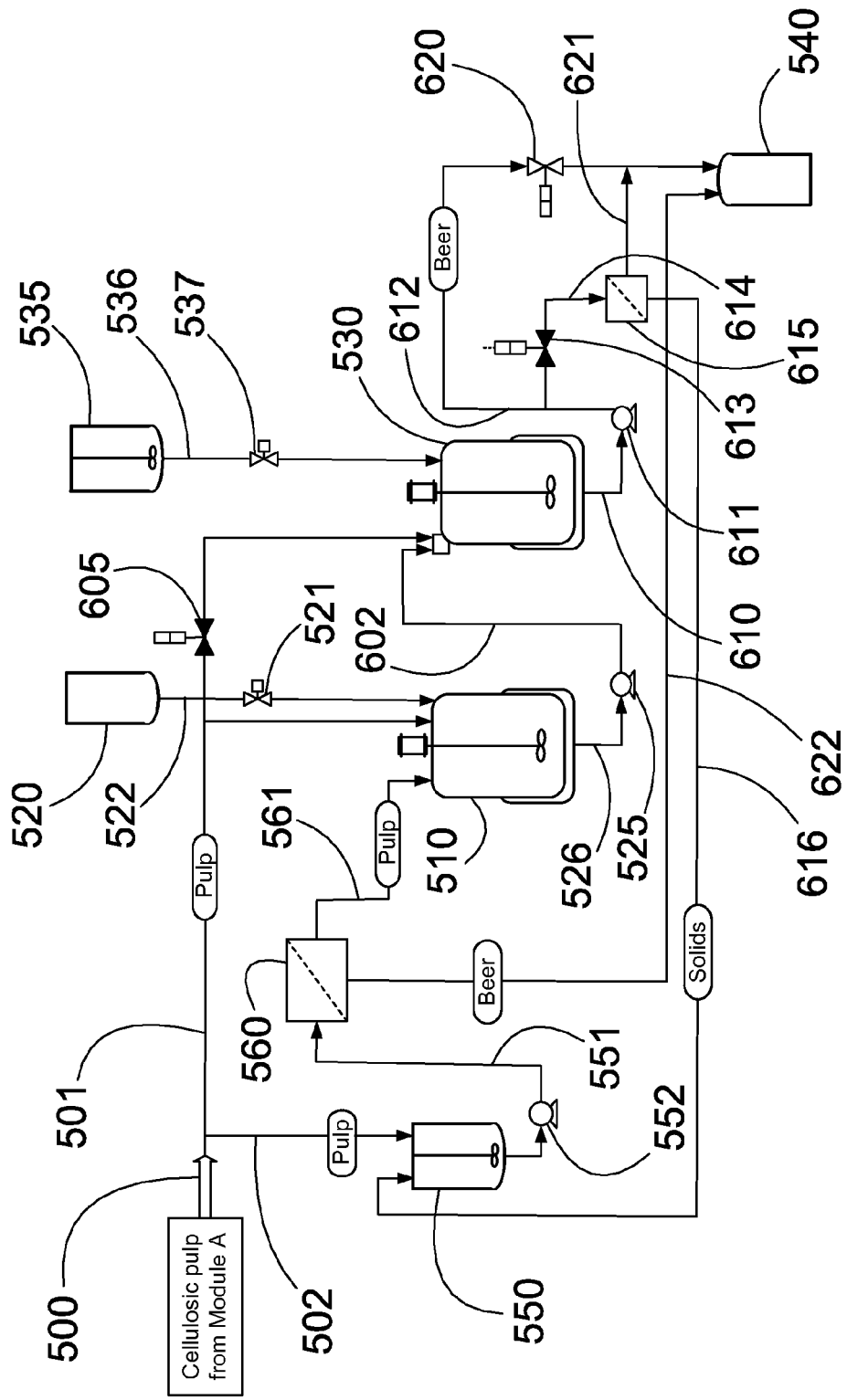
FIG. 9 is a schematic flowchart showing another exemplary optional systems design for a hybrid saccharification and fermentation module generally configured for receiving and processing therein a cellulosic solids stream according to an exemplary embodiment of the modular biorefinery of the present invention, wherein the optional systems design is configured for recovery and recycling of hydrolytic enzymes from a fermentation tank.

According to another aspect, an exemplary enzyme recovery and recycling system may be configured to cooperate with an HSF system wherein the hydrolytic enzymes are recovered from beer egressing from a fermentation tank. An illustrative schematic flowchart generally outlining this aspect is shown in FIG. 9 wherein a cellulosic pulp stream 500 recovered from a first module A, is delivered to a saccharification tank 510 via a suitable pipeline 501. A suitable preparation comprising fresh hydrolytic enzymes is delivered to the saccharification tank 510 via line 522 from an enzyme holding tank 520. The delivery of the enzyme preparation to the saccharification tank is controllable by valve 521 interposed line 522. After a suitable time period of saccharification in the saccharification tank 510 under suitable physical conditions (i.e., temperature and pressure), the hydrolysate comprising a solubilized carbohydrates stream and digested solids is transferred from the saccharification tank 510 to the fermentation tank 530 via outlet line 526 with the aid of a pump 526. A suitable inoculum comprising fermentative microorganisms is controllably delivered to the fermentation tank 530 via line 536 and valve 437 from a holding tank 535. After fermentation has proceeded for a suitable period of time, the fermentation beer and spent solids are recovered from the fermentation tank 530 via outlet lines 610, 612 with the aid of a pump 611 and are transferred to a fermentation beer storage tank 540. Those skilled in these arts will understand that in this HSF system configuration, a large portion of the hydrolytic enzymes added to saccharification tank 510 will be attached to the spent solids recovered from the fermentation tank 530 and the remainder will be distributed throughout the fermentation beer. The flow of the fermentation beer and digested solids from the fermentation tank 530 to the fermentation beer storage tank 540 is controllable and manipulable by diverter valves 613, 620. A portion of the flow of the fermentation beer and digested solids may be optionally be diverted to a solid/liquid separation unit 615 wherefrom the liquids are transferred via line 621 to the fermentation beer storage tank 540 wherein they are commingled with the fermentation beer stream delivered by line 612. The settled solids are transferred via line 616 to an enzyme recovery tank 550 where the settled solids with enzymes attached thereto are reconditioned by commingling and intermixing with fresh cellulosic pulp stream 500 via pipeline 502. The reconditioned enzyme solids stream is transferred via pipeline 551 by pump 552 to a solid/liquid separation tank 560 from where the reconditioned enzyme solids stream is transferred via pipeline 561 back to the saccharification tank for hydrolysis of fresh cellulosic pulp stream 500 via pipeline 501. Additional fresh enzymes may be controllably added, if so desired, to the saccharification tank 510 from the fresh enzyme holding tank 520 via line 522. The separated fermentation beer resulting from settling of the reconditioned enzyme solids stream in the solid/liquid separation tank 560 is transferred via line 622 to the fermentation beer storage tank 540. The fermentation beer is subsequently transferred from the fermentation beer holding tank 540 for further processing and refining as described elsewhere herein.

Figure 10:
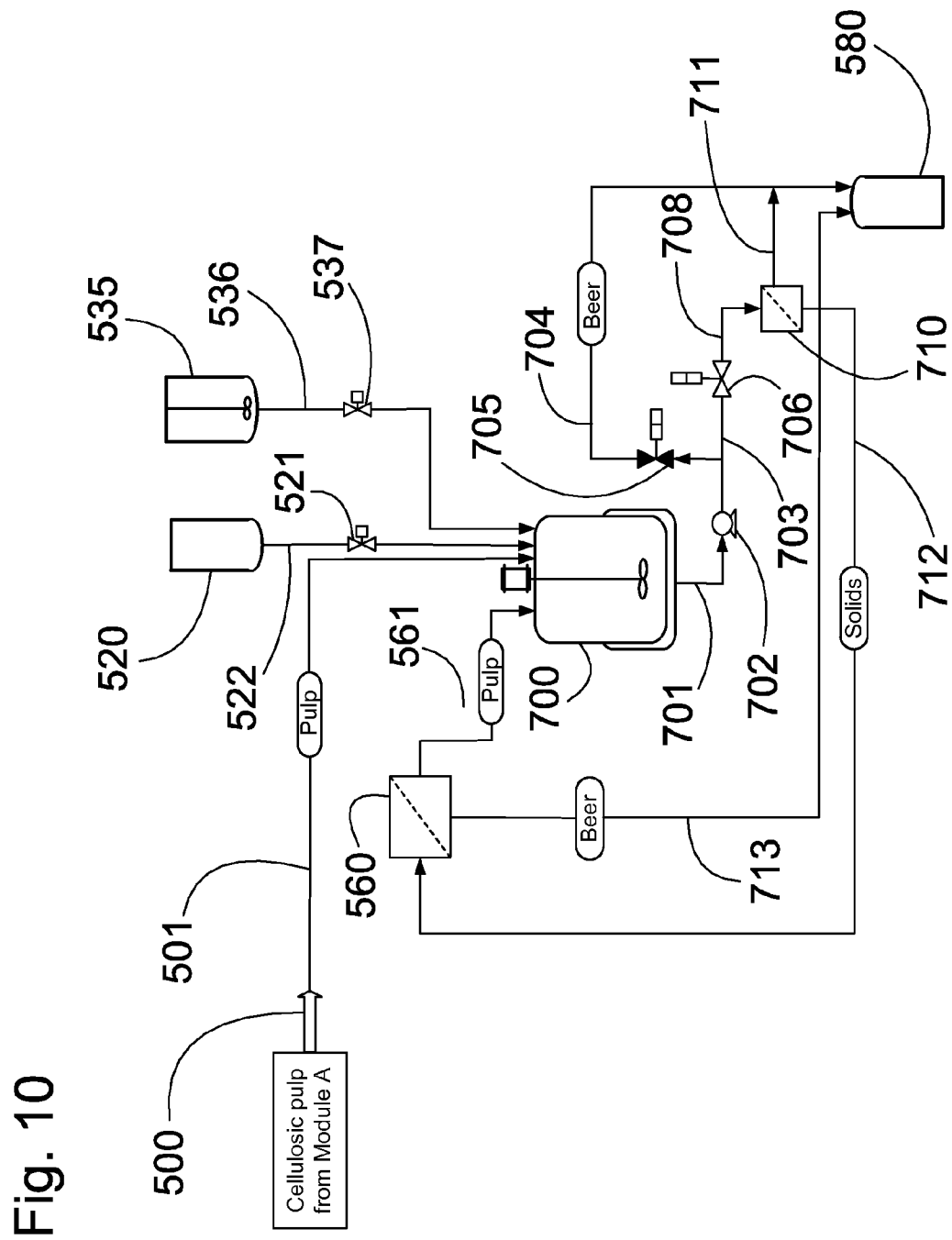
FIG. 10 is a schematic flowchart showing an exemplary optional systems design for a simultaneous saccharification and fermentation module generally configured for receiving and processing therein a cellulosic solids stream according to an exemplary embodiment of the modular biorefinery of the present invention, wherein the optional systems design is configured for recovery and recycling of hydrolytic enzymes from a saccharification/fermentation tank.

According to another aspect, the hydrolytic enzymes are recoverable from beer egressing from a tank containing therein simultaneous saccharification and fermention (SSF) processes. An illustrative schematic flowchart generally outlining this aspect is shown in FIG. 10 wherein a cellulosic pulp stream 500 recovered from a first module A, is delivered to a saccharification/fermentation tank 700 via pipeline 501. A suitable preparation comprising fresh hydrolytic enzymes is delivered to the saccharification/fermentation tank 700 via line 522 from an enzyme holding tank 520. The delivery of the enzyme preparation to the saccharification/fermentation tank 700 is controllable by valve 521 interposed line 522. A suitable inoculum comprising fermentative microorganisms is controllably delivered to the saccharification/fermentation tank 700 via line 536 and valve 437 from a holding tank 535. After a suitable time period of saccharification and fermentation under suitable physical conditions (i.e., temperature and pressure), the fermentation beer and spent solids are recovered from the saccharification/fermentation tank 700 via outlet line 701 with the aid of a pump 702 and are transferred to a fermentation beer storage tank 580. Those skilled in these arts will understand that in this SSF system configuration, a large portion of the hydrolytic enzymes added to saccharification/fermentation tank 700 will be attached to the recovered spent solids and the remainder will be distributed throughout the fermentation beer.

The flow of the hydrolysate and digested solids from the saccharification tank 510 to the fermentation tank is controllable and manipulable by diverter valves 705, 706. A portion of the flow of the hydrolysate and digested solids may be optionally be diverted to a solid/liquid separation unit 710 wherefrom the liquids are transferred via line 711 to the fermentation tank 530 wherein they are commingled with the liquid carbohydrates hydrolysate stream delivered by line 704. The settled solids are transferred via line 712 to a solid/liquid separation tank 560 from where the reconditioned enzyme solids stream is allowed to further settle after which the settled enzyme solids stream is transferred via pipeline 561 back to the saccharification tank for hydrolysis of fresh cellulosic pulp stream 500 via pipeline 501. Additional fresh enzymes may be controllably added, if so desired, to the saccharification tank 510 from the fresh enzyme holding tank 520 via line 522. Additional fresh fermentative microorganisms is controllably delivered to the saccharification/fermentation tank 700 via line 536 and valve 437 from the holding tank 535. The separated fermentation beer resulting from additional settling of the enzyme solids stream in the solid/liquid separation tank 560 is transferred via line 713 to the fermentation beer storage tank 580. The fermentation beer is subsequently transferred from the fermentation beer holding tank 580 for further processing and refining as described elsewhere herein.

The systems, methods and processes for fractionating lignocellulosic feedstocks into component parts which are then subsequently separated are described in more detail in the following examples with a selected hardwood and a selected softwood species. The following examples are intended to be exemplary of the invention and are not intended to be limiting.

EXAMPLE 1

Representative samples of whole logs of British Columbian aspen (Populus tremula) (~125 years old) were collected. After harvesting, logs were debarked, split, chipped, and milled to a chip size of approximately ≦10 mm×10 mm×3 mm. Chips were stored at room temperature (moisture content at equilibrium was ~10%). The aspen chips were organosolv-pretreated in aqueous ethanol (50% w/w ethanol) with no addition of exogenous acid or base, in a 2-L Parr® reactor (Parr is a registered trademark of the Parr Instrument Company, Moline, Ill., USA). Duplicate 200 g (ODW) samples of the aspen chips, designated as ASP1, were cooked at 195° C. for 60 min. The liquor:wood ratio was 5:1 weight-based. After cooking, the reactor was cooled to room temperature. Solids and the spent liquor were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of washed and unwashed pulps was determined according to a modified Klason lignin method derived from the Technical Association of Pulp and Paper Industry (TAPPI) standard method T222 om-88 (TAPPI methods in CD-ROM, 2004, TAPPI Press). Liquids were analyzed for carbohydrate degradation products (furfural, 5-hydroxymethylfurfural), organic acids, and oligo- and monosaccharides according to standard procedures established by the National Renewable Energy Laboratory (NREL, Golden, Colo., USA). The resulting data were used to calculate overall lignin and carbohydrate recoveries and process mass balance. The carbohydrate composition and overall carbohydrate recoveries from the raw and pretreated aspen chips are shown in Table 1. 222.2 g (oven-dried weight, odw) of ASP1 pulp were recovered after batch organosolv processing of 400 g of aspen wood chips (55.6% pulp yield) containing mainly fermentable-into-ethanol carbohydrates. Pentoses and hexoses were partially degraded resulting in 0.71 g Kg$^{-1}$ of furfural and 0.06 g Kg$^{-1}$ of 5-HMF, respectively. The different classes of lignins recovered from the pulp and liquors are shown in Table 2.

TABLE 1

Carbohydrate content of raw and pretreated aspen chips (ASP1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 0.44 | 1.75 | 0.04 | 0.17 | 0.21 | 9.69 | 2.53 | 12.23 |
| Galactan | 0.43 | 1.71 | 0.16 | 0.26 | 0.42 | 15.16 | 9.07 | 24.23 |
| Glucan | 48.76 | 195.03 | 185.40 | 0.32 | 185.72 | 0.16 | 95.06 | 95.23 |
| Xylan | 16.44 | 65.75 | 17.60 | 8.70 | 26.30 | 13.23 | 26.77 | 40.00 |
| Mannan | 1.48 | 5.92 | 4.62 | 0 | 4.62 | 0 | 78.02 | 78.02 |
| Total: | 67.55 | 270.16 | 207.82 | 9.45 | 217.27 | | | |

TABLE 2

Lignin input in raw aspen chips and lignin fractions recovered after organosolv pretreatment (ASP1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 91.35 | — | — |
| Self-precipitated lignin (HMW) | — | — | 9.60 |
| Precipitated lignin* (MMW) | — | — | 32.12 |
| Very low molecular wt. lignin (VLMW) | — | — | 11.72 |
| Residual lignin (VHMW) | — | 11.33 | — |
| Total: | 91.35 | 11.33 | 53.44 |

*recovered from the liquor by precipitation with water; AIL—acid-insoluble lignin; ASL—acid-soluble lignin The potential of the washed pulp for production of ethanol was evaluated in 100-mL Erlenmeyer flasks. The pH of the washed pulp was first adjusted with a water ammonia solution to pH 5.50, then placed into Erlenmeyer flasks and resuspended in distilled water to a total reaction weight of 100 g (including the yeast and enzyme weight, the final reaction volume was ~100 mL) and a final solids concentration of 16% (w/w). The ethanol production process was run according to a simultaneous saccharification and fermentation scheme (SSF) using a fungal cellulase preparation containing all of the enzyme activities required to depolymerize cellulose at 15 FPU g$^{-1}$ glucan supplemented with a fungal beta-glucosidase preparation (30 CBU g$^{-1}$ glucan) and a ethanologenic yeast, *Saccharomyces cerevisiae* strain Y-1528 (available from the Agricultural Research Service, United States Department of Agriculture, Peoria, Ill., USA) at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 39.40% theoretical ethanol yield based on initial hexose input. The final ethanol beer concentration was 3.26% (w/w) (FIGS. 11a and 11b).

EXAMPLE 2

Duplicate 200-g samples of the wood chips prepared in Example 1, designated as ASP2, were used for this study. The aspen chips were organosolv-pretreated in aqueous ethanol (50% w/w ethanol) with no addition of exogenous acid or base, in a 2-L Parr® reactor. Duplicate 200 g (ODW) samples of aspen chips were cooked at 195° C. for 90 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88 (TAPPI methods in CD-ROM, 2004, TAPPI Press). Liquids were analyzed for carbohydrate degradation products (furfural, 5-hydromethylfurfural), acids, and oligo- and monosaccharides according to standard procedures established by the National Renewable Energy Laboratory (NREL, Golden, Colo., USA). The resulting data were used to calculate overall carbohydrate and lignin recoveries and process mass balance. The carbohydrate composition and overall carbohydrate recoveries from the raw and pretreated aspen chips are shown in Table 3. 230.2 g (odw) of pulp were recovered after batch organosolv processing of 400 g of aspen wood chips (57.6% pulp yield), and comprised mainly fermentable-into-ethanol carbohydrates. Pentoses and hexoses were partially degraded resulting in 0.53 g $Kg^{-1}$ of furfural and 0.05 g $Kg^{-1}$ of 5-HMF, respectively. The lignin content in the raw aspen chips and overall lignin recovery after pretreatment are shown in Table 4.

Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, then placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a SSF using a fungal cellulase preparation containing all of the enzyme activities required to depolymerize cellulose at 15 FPU $g^{-1}$ glucan supplemented with a fungal beta-glucosidase preparation (30 CBU $g^{-1}$ glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 79.30% theoretical ethanol yield based on initial hexose input. The final ethanol beer concentration was 6.33% (w/w) (FIGS. 11a and 11b).

EXAMPLE 3

Duplicate 200-g samples of the wood chips prepared in Example 1, designated as ASP3, were used for this study. The aspen chips were organosolv-pretreated in aqueous ethanol (50% w/w ethanol) with no addition of exogenous acid or base, in a 2-L Parr® reactor. The duplicate samples of aspen chips were cooked in duplicate at 195° C. for 120 min. The

TABLE 3

Carbohydrate content of raw and pretreated aspen chips (ASP2 pretreatment conditions) and overall carbohydrate recovery

| Component | Raw Chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 0.44 | 1.75 | 0 | 0.22 | 0.22 | 12.54 | 0.00 | 12.54 |
| Galactan | 0.43 | 1.71 | 0 | 0.21 | 0.21 | 12.25 | 0.00 | 12.25 |
| Glucan | 48.76 | 195.03 | 194.50 | 0.37 | 194.87 | 0.19 | 99.73 | 99.92 |
| Xylan | 16.44 | 65.75 | 14.80 | 6.76 | 21.56 | 10.28 | 22.51 | 32.79 |
| Mannan | 1.48 | 5.92 | 4.07 | 0.34 | 4.41 | 5.74 | 68.78 | 74.52 |
| Total: | 67.55 | 270.16 | 213.37 | 7.9 | 221.27 | | | |

TABLE 4

Lignin input in raw aspen chips and lignin fractions recovered after organosolv pretreatment (ASP2 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 91.35 | — | — |
| Self-precipitated lignin (HMW) | — | — | 9.14 |
| Precipitated lignin* (MMW) | — | — | 43.09 |
| Very low molecular wt. lignin (VLMW) | — | — | 12.60 |
| Residual lignin (VHMW) | — | 7.32 | — |
| Total: | 91.35 | 7.32 | 64.83 |

*recovered from the liquor by precipitation with water; AIL—acid-insoluble lignin; ASL—acid-soluble lignin liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and overall carbohydrate recoveries from the raw and pretreated aspen chips are shown in Table 5.

219.9 g (odw) of pulp were recovered after batch organosolv processing of 400 g of aspen wood chips (54.98% pulp yield) containing mainly fermentable-into-ethanol carbohydrates. Pentoses and hexoses were partially degraded resulting in 0.92 g $Kg^{-1}$ of furfural and 0.08 g $Kg^{-1}$ of 5-HMF, respectively. The lignin contents in raw aspen chips and overall lignin recovery after pretreatment are shown in Table 6.

Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a SSF scheme using a fungal cellulase preparation containing all of the enzyme activities required to depolymerize cellulose at 15 FPU $g^{-1}$ glucan supplemented with a fungal beta-glucosidase preparation (30 CBU $g^{-1}$ glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 79.00% theoretical ethanol yield based on initial hexose input. The final ethanol beer concentration was 6.60% (w/w) (FIGS. 11*a* and 11*b*).

EXAMPLE 4

Representative samples of British Columbian beetle-killed lodgepole pine (*Pinus contorta*) sapwood (~120 years old) were collected. After harvesting, logs were debarked, split, chipped, and milled to a chip size of approximately $\leq 10$ mm×10 mm×3 mm. Chips were stored at room temperature (moisture content at equilibrium was ~10%). Duplicate 200-g samples of these wood chips, designated as BKLLP1, were used for this study. The chips were organosolv-pretreated in aqueous ethanol (50% w/w ethanol) with addition of 1.10% (w/w) sulfuric acid, in a 2-L Parr® reactor. The chips were cooked in duplicate at 170° C. for 60 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The obtained data were used to calculate overall carbohydrate and lignin recoveries and process mass balance. The carbohydrate composition and the overall carbohydrate recoveries from the raw and pretreated beetle-killed lodgepole pine chips are shown in Table 7. 177.2 g (odw) of pulp were recovered after batch organosolv processing of 400 g of wood chips (44.30% pulp yield) containing mainly fermentable-into-ethanol carbohydrates. Pentoses and hexoses were partially degraded resulting in 0.72 g $Kg^{-1}$ of furfural and 1.78 g $Kg^{-1}$ of 5-HMF, respectively. The lignin content in raw beetle-killed lodgepole pine chips and overall lignin recovery after pretreatment are shown in Table 8.

TABLE 5

Carbohydrate content of raw and pretreated aspen chips (ASP3 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 0.44 | 1.75 | 0 | 0.10 | 0.10 | 5.70 | 0 | 5.70 |
| Galactan | 0.43 | 1.71 | 0 | 0.15 | 0.15 | 8.75 | 0 | 8.75 |
| Glucan | 48.76 | 195.03 | 186.63 | 0.33 | 186.96 | 0.17 | 95.69 | 95.86 |
| Xylan | 16.44 | 65.75 | 12.56 | 4.03 | 16.59 | 6.13 | 19.10 | 25.23 |
| Mannan | 1.48 | 5.92 | 3.50 | 0.30 | 3.80 | 5.06 | 59.02 | 64.08 |
| Total: | 67.55 | 270.16 | 202.69 | 4.91 | 207.6 | | | |

TABLE 6

Lignin input in raw aspen chips and lignin fractions recovered after organosolv pretreatment (ASP3 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 91.35 | — | — |
| Self-precipitated lignin (HMW) | — | — | 0.16 |
| Precipitated lignin* (MMW) | — | — | 40.70 |
| Very low molecular wt. lignin (VLMW) | — | — | 11.46 |
| Residual lignin (VHMW) | — | 6.47 | — |
| Total: | 91.35 | 6.47 | 52.32 |

*recovered from the liquor by precipitation with water; AIL—acid-insoluble lignin; ASL—acid-soluble lignin

TABLE 7

Carbohydrate content of raw and pretreated beetle-killed lodgepole pine chips (BKLLP1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 1.76 | 7.03 | 0.05 | 0.77 | 0.82 | 10.96 | 0.76 | 11.72 |
| Galactan | 2.01 | 8.05 | 0.35 | 1.25 | 1.60 | 15.52 | 4.40 | 19.92 |
| Glucan | 45.55 | 182.22 | 150.44 | 4.37 | 154.81 | 2.40 | 82.56 | 84.96 |
| Xylan | 7.22 | 28.90 | 3.58 | 1.64 | 5.22 | 5.68 | 12.39 | 18.07 |
| Mannan | 11.07 | 44.29 | 6.06 | 0.00 | 6.06 | 0.00 | 13.68 | 13.68 |
| Total: | 67.61 | 270.49 | 160.48 | 8.03 | 168.51 | | | |

TABLE 8

Lignin input in raw beetle-killed lodgepole pine chips and lignin fractions recovered after organosolv pretreatment (BKLLP1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 106.85 | — | — |
| Self-precipitated lignin (HMW) | — | — | 0.17 |
| Precipitated lignin* (MMW) | — | — | 28.10 |
| Very low molecular wt. lignin (VLMW) | — | — | 13.47 |
| Residual lignin (VHMW) | — | 15.29 | — |
| Total: | 106.85 | 15.29 | 41.74 |

*recovered from the liquor by precipitation with water; AIL—acid-insoluble lignin; ASL—acid-soluble lignin Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a simultaneous saccharification and fermentation scheme (SSF) using a fungal cellulase preparation containing all of the enzyme activities required to depolymerize cellulose at 15 FPU $g^{-1}$ glucan supplemented with a fungal beta-glucosidase preparation (30 CBU $g^{-1}$ glucan) together with an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 60.50% theoretical ethanol yield based on initial hexose input. The final ethanol beer concentration was 7.18% (w/w) (FIGS. 12a and 12b).

EXAMPLE 5

Duplicate 200-g samples British Columbian beetle-killed lodgepole pine (*Pinus contorta*), designated as BKLLP2, of the chips prepared for the study described in the Example 4, were organosolv-pretreated in aqueous ethanol (50% w/w ethanol) with addition of 1.10% (w/w) sulphuric acid, in a 2-L Parr® reactor. Duplicate 200-g (ODW) samples of chips were cooked at 175° C. for 60 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated beetle-killed lodgepole pine chips are shown in Table 9. 144.4 g (odw) of pulp were recovered after batch organosolv processing of 400 g of wood chips (36.10% pulp yield) containing mainly fermentable-into-ethanol carbohydrates. Pentoses and hexoses were partially degraded resulting in 0.92 g $Kg^{-1}$ of furfural and 1.87 g $Kg^{-1}$ of 5-HMF, respectively. The lignin content in raw beetle-killed lodgepole pine chips and overall lignin recovery after pretreatment are shown in Table 10.

TABLE 9

Carbohydrate content of raw and pretreated beetle-killed lodgepole pine chips (BKLLP2 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 1.76 | 7.03 | 0.04 | 0.39 | 0.43 | 5.55 | 0.62 | 6.17 |
| Galactan | 2.01 | 8.05 | 0.03 | 0.79 | 0.82 | 9.81 | 0.36 | 10.17 |

TABLE 9-continued

Carbohydrate content of raw and pretreated beetle-killed lodgepole pine chips (BKLLP2 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Glucan | 45.55 | 182.22 | 134.08 | 5.28 | 139.36 | 2.90 | 73.58 | 76.48 |
| Xylan | 7.22 | 28.90 | 1.59 | 0.65 | 2.24 | 2.25 | 5.50 | 7.75 |
| Mannan | 11.07 | 44.29 | 2.30 | 0 | 2.30 | 0 | 5.18 | 5.18 |
| Total: | 67.61 | 270.49 | 138.04 | 7.11 | 145.15 | | | |

TABLE 10

Lignin input in raw beetle-killed lodgepole pine chips and lignin fractions recovered after organosolv pretreatment (BKLLP2 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 106.85 | — | — |
| Self-precipitated lignin (HMW) | — | — | 0.13 |
| Precipitated lignin* (MMW) | — | — | 33.01 |
| Very low molecular wt. lignin (VLMW) | — | — | 11.88 |
| Residual lignin (VHMW) | — | 7.15 | — |
| Total: | 106.85 | 7.15 | 45.02 |

*recovered from the liquor by precipitation with water; AIL—acid-insoluble lignin; ASL—acid-soluble lignin Production of ethanol from the washed pulp was evaluated in 100-mL Erlenmeyer flasks. The experiments were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a simultaneous saccharification and fermentation scheme (SSF) using a fungal cellulase preparation containing all of the enzyme activities required to depolymerize cellulose at 15 FPU $g^{-1}$ glucan supplemented with a fungal beta-glucosidase preparation (30 CBU $g^{-1}$ glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 53.10% theoretical ethanol yield based on initial hexose input. The final ethanol beer concentration was 7.74% (w/w) (FIGS. 12a and 12b).

EXAMPLE 6

Duplicate 200-g samples British Columbian beetle-killed lodgepole pine (*Pinus contorta*), designated as BKLLP3, chips prepared for the study described in the Example 4, were organosolv-pretreated in aqueous ethanol (50% w/w ethanol) with addition of 1.10% (w/w) sulphuric acid, in a 2-L Parr® reactor chips were cooked in duplicate at 180° C. for 60 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated beetle-killed lodgepole pine chips are shown in Table 11. 120.7 g (odw) of pulp was recovered after batch organosolv processing of 400 g of wood chips (30.18% pulp yield) containing mainly fermentable into ethanol carbohydrates. Pentoses and hexoses were partially degraded resulting in 1.47 g $Kg^{-1}$ of furfural and 2.17 g $Kg^{-1}$ of 5-HMF, respectively. The lignin content in raw aspen chips and overall lignin recovery after pretreatment are shown in Table 12.

TABLE 11

Carbohydrate content of raw and pretreated beetle-killed lodgepole pine chips (BKLLP3 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 1.76 | 7.03 | 0.04 | 0.22 | 0.26 | 3.13 | 0.52 | 3.65 |
| Galactan | 2.01 | 8.05 | 0.33 | 0.61 | 0.94 | 7.57 | 4.05 | 11.62 |
| Glucan | 45.55 | 182.22 | 102.34 | 6.15 | 108.49 | 3.38 | 56.16 | 59.54 |

TABLE 11-continued

Carbohydrate content of raw and pretreated beetle-killed lodgepole pine chips (BKLLP3 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Xylan | 7.22 | 28.90 | 2.34 | 0.41 | 2.75 | 1.42 | 8.10 | 9.52 |
| Mannan | 11.07 | 44.29 | 3.86 | 2.07 | 5.93 | 4.67 | 8.72 | 13.39 |
| Total: | 67.61 | 270.49 | 108.91 | 9.46 | 118.37 | | | |

TABLE 12

Lignin input in raw beetle-killed lodgepole pine chips and lignin fractions recovered after organosolv pretreatment (BKLLP3 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 106.85 | — | — |
| Self-precipitated lignin (HMW) | — | — | 0.26 |
| Precipitated lignin* (MMW) | — | — | 33.64 |
| Very low molecular wt. lignin (VLMW) | — | — | 15.33 |
| Residual lignin (VHMW) | — | 9.11 | — |
| Total: | 106.85 | 9.11 | 49.23 |

*recovered from the liquor by precipitation with water; AIL—acid-insoluble lignin; ASL—acid-soluble lignin Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a SSF scheme using a fungal cellulase preparation containing all of the enzyme activities required to depolymerize cellulose at 15 FPU $g^{-1}$ glucan supplemented with a fungal beta-glucosidase preparation (30 CBU $g^{-1}$ glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 44.60% theoretical ethanol yield based on initial hexose input. The final ethanol beer concentration was 7.79% (w/w) (FIGS. 12a and 12b).

EXAMPLE 7

Representative samples of wheat straw (*Triticum* sp.) from Eastern Washington, USA were collected. Wheat straw was cut into ~5-cm chips and stored at room temperature (moisture content at equilibrium was ~10%). The straw was organosolv-pretreated in aqueous ethanol (50% w/w ethanol) with no addition of exogenous acid or base, in a 2-L Parr® reactor. Duplicate 100-g (ODW) samples of wheat straw, designated as WS-1, were cooked in duplicate at 195° C. for 90 min. The liquor:raw material ratio was 10:1 (w/w). After cooking, the reactor was cooled to room temperature. Solids and the spent liquor were then separated by filtration. Solids were intensively washed with a hot ethanol solution (70° C.) followed by a tap water wash step. The moisture content of the washed pulp was reduced to about 50% with the help of a hydraulic press (alternatively a screw press can be used). The washed pulp was homogenized and stored in a fridge at 4° C. The chemical compositions (hexose, pentose, lignin content) of washed and unwashed pulps were determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated wheat straw are shown in Table 13. 46.8 g (oven-dried weight, odw) of WS-1 pulp was recovered after batch organosolv processing of 100 g of wheat straw (46.8% pulp yield) containing mainly fermentable-into-ethanol carbohydrates. Pentoses and hexoses were partially degraded resulting in 0.39 g $Kg^{-1}$ of furfural and 0.03 g $Kg^{-1}$ of 5-HMF, respectively. The lignin content in raw wheat straw and overall lignin recovery after pretreatment are shown in Table 14.

TABLE 13

Carbohydrate content of raw and pretreated wheat straw chips (WS-1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 3.85 | 3.85 | 0.00 | 0.17 | 0.17 | 4.39 | 0.00 | 4.39 |
| Galactan | 1.16 | 1.16 | 0.00 | 0.19 | 0.19 | 16.72 | 0.00 | 16.72 |

TABLE 13-continued

Carbohydrate content of raw and pretreated wheat straw chips (WS-1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Glucan | 54.92 | 54.92 | 35.47 | 0.00 | 35.47 | 0.00 | 64.58 | 64.58 |
| Xylan | 27.83 | 27.83 | 3.36 | 2.68 | 6.03 | 9.62 | 12.06 | 21.67 |
| Mannan | 0.53 | 0.53 | 0.00 | 0.08 | 0.08 | 15.78 | 0.00 | 15.78 |
| Total: | 88.30 | 88.30 | 38.83 | 3.12 | 41.94 | | | |

TABLE 14

Lignin input in raw wheat straw chips and lignin fractions recovered after organosolv pretreatment (WS-1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 17.44 | — | — |
| Self-precipitated lignin (HMW) | — | — | 1.7 |
| Precipitated lignin* (MMW) | — | — | 8.4 |
| Very low molecular wt. lignin (VLMW) | — | — | — |
| Residual lignin (VHMW) | — | 4.31 | — |
| Total: | 17.44 | 4.31 | 10.1 |

*recovered from the liquor by precipitation with water; AIL—acid-insoluble lignin; ASL—acid-soluble lignin The potential of the produced washed wheat straw pulp for production of ethanol was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the final reaction volume was ~100 mL) and a final solids concentration of 16% (w/w). The ethanol process was run according to a SSF scheme using a fungal cellulase preparation containing all of the enzyme activities required to depolymerize cellulose at 15 FPU $g^{-1}$ glucan supplemented with a fungal beta-glucosidase preparation (30 CBU $g^{-1}$ glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 88.86% theoretical ethanol yield based on initial hexose input. The final ethanol beer concentration was 6.14% (w/w) (FIGS. 13a and 13b).

EXAMPLE 8

Representative samples of switchgrass (*Panicum virgatum*) from Tennessee, USA were collected. The switchgrass samples were cut to a particle size of approximately 5 cm and stored at room temperature (moisture content at equilibrium was ~10%). The switchgrass chips were organosolv-pretreated in aqueous ethanol (50% w/w ethanol) with no addition of exogenous acid or base, in a 2-L Parr® reactor. Dubplicate 100-g (odw) switchgrass samples designated as SWG-1, were cooked at 195° C. for 90 min. The liquor:raw material ratio was 10:1 (w/w). After cooking, the reactor was cooled to room temperature. Solids and the spent liquor were then separated by filtration. Solids were intensively washed with a hot ethanol solution (70° C.) followed by a tap water wash step. The moisture content of the washed pulp was reduced to about 50% with the help of a hydraulic press (alternatively a screw press can be used). The washed pulp was homogenized and stored in a fridge at 4° C. The chemical composition (hexose, pentose, lignin content) of washed and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated switchgrass are illustrated in Table 15. 45.2 g (oven-dried weight, odw) of SWG-1 pulp was recovered after batch organosolv processing of 100 g of switchgrass (45.2% pulp yield) containing mainly fermentable-into-ethanol carbohydrates. Pentoses and hexoses were partially degraded resulting in 0.917 g $Kg^{-1}$ of furfural and 0.21 g $Kg^{-1}$ of 5-HMF, respectively. The lignin content in raw switchgrass and overall lignin recovery after pretreatment are shown in Table 16.

TABLE 15

Carbohydrate content of raw and pretreated switchgrass particles (SWG-1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 3.44 | 3.44 | 0.00 | 0.23 | 0.23 | 6.79 | 0.00 | 6.79 |
| Galactan | 0.93 | 0.93 | 0.00 | 0.18 | 0.18 | 19.48 | 0.00 | 19.48 |

TABLE 15-continued

Carbohydrate content of raw and pretreated switchgrass particles
(SWG-1 pretreatment conditions) and overall carbohydrate recovery

| | Raw chips (%) | Raw Feedstock Input (g) | Pretreated Feedstock Output | | | Carbohydrates Recovery | | |
|---|---|---|---|---|---|---|---|---|
| Component | | | Pulp (g) | Liquor (g) | Total (g) | Soluble (%) | Insoluble (%) | Total (%) |
| Glucan | 51.04 | 51.04 | 35.88 | 1.37 | 37.25 | 2.68 | 70.31 | 72.99 |
| Xylan | 26.69 | 26.69 | 5.37 | 3.01 | 8.39 | 11.29 | 20.14 | 31.43 |
| Mannan | 0.00 | 0.00 | 0.00 | 0.00 | 0.00 | 0.00 | 0.00 | 0.00 |
| Total: | 82.10 | 82.10 | 41.26 | 4.80 | 46.05 | | | |

TABLE 16

Lignin input in raw switchgrass particles and
lignin fractions recovered after organosolv pretreatment
(SWG-1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 18.17 | — | — |
| Self-precipitated lignin (HMW) | — | — | 3.00 |
| Precipitated lignin* (MMW) | — | — | 10.6 |
| Very low molecular wt. lignin (VLMW) | — | — | — |
| Residual lignin (VHMW) | — | 2.67 | — |
| Total: | 18.17 | 2.67 | 13.60 |

*recovered from the liquor by precipitation with water; AIL—acid-insoluble lignin; ASL—acid-soluble lignin The potential of the produced washed switchgrass pulp for production of ethanol was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the final reaction volume was ~100 mL) and a final solids concentration of 16% (w/w). The ethanol process was run according to a SSF scheme using a fungal cellulase preparation containing all of the enzyme activities required to depolymerize cellulose at 15 FPU $g^{-1}$ glucan supplemented with a fungal beta-glucosidase preparation (30 CBU $g^{-1}$ glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 82.51% theoretical ethanol yield based on initial hexose input. The final ethanol beer concentration was 5.97% (w/w) (FIGS. 13a and 13b).

While this invention has been described with respect to the exemplary embodiments, those skilled in these arts will understand how to modify and adapt the systems, processes and equipment configurations disclosed herein for continuously receiving and controllably commingling lignocellulosic feedstocks with counter-flowing organic solvents. Certain novel elements disclosed herein for processing a continuous incoming stream of lignocellulosic feedstocks with countercurrent flowing or alternatively, concurrent flowing organic solvents for separating the lignocellulosic materials into component parts and further processing thereof, can be modified for integration into batch systems configured for processing lignocellulosic materials. For example, the black liquors produced in batch systems may be de-lignified and then a portion of the de-lignified black liquor used to pretreat a new, fresh batch of lignocellulosic materials prior to batch organosolv cooking, while the remainder of the de-lignified black liquor is further processed into component parts as disclosed herein. Specifically, the fresh batch of lignocellulosic materials maybe controllably commingled with portions of the de-lignified black liquor for selected periods of time prior to contacting, commingling and impregnating the batch of lignocellulosic materials with suitable organic solvents. Also, it is within the scope of the present invention, to provide turbulence within a batch digestion system wherein a batch of lignocellulosic materials is cooked with organic solvents by providing pressurized flows of the organic solvents within and about the digestion vessel. It is optional to controllably remove portions of the organic solvent/black liquors from the digestion vessel during the cooking period and concurrently introduce fresh organic solvent and/or de-lignified black liquors thereby facilitating and expediting delignification of the lignocellulosic materials. It is also within the scope of the present invention to further process the de-lignified black liquors from the batch lignocellulosic digestion systems to separate and further process components parts exemplified by lignins, furfural, acetic acid, monosaccharides, oligosaccharides, and ethanol among others.

What is claimed is:

1. A modular biorefining process for separating a lignocellulosic feedstock into component parts and further processing of said component parts; the modular process comprising:

a first processing module provided with a first series of steps for receiving, physically screening, and physico-chemically fractionating a lignocellulosic feedstock with an organic solvent separately provided thereto thereby extracting component parts therefrom, and separating said component parts into a first liquid fraction and a cellulosic solids fraction comprising a plurality of a first class of lignin derivatives therein;

a second processing module provided with a second series of steps for receiving therein said cellulosic solids fraction, de-lignifying said cellulosic solids fraction, and recovering therefrom a delignified cellulosic solids fraction;

a third processing module provided with a third series of steps comprising:
 separating a first solids fraction from the first liquid fraction thereby producing a second liquid fraction, said first solids fraction comprising a plurality of a second class of lignin derivatives;

separating a second solids fraction from the second liquid fraction thereby producing a third liquid fraction, said second solids fraction comprising a plurality of a third class of lignin derivatives;

recovering from the third liquid fraction at least a portion of the organic solvent and a processed third liquid fraction; and a fourth processing module provided with at least one step for recovery of a first semi-solid waste material therefrom said processed third liquid fraction.

2. A modular biorefining process according to claim 1, wherein the second series of steps comprises steps for controllably reducing the viscosity of the de-lignified cellulosic solids fraction, controllably digesting the reduced-viscosity de-lignified cellulosic solids fraction, and recovering therefrom a fourth liquid fraction comprising at least soluble sugars.

3. A modular biorefining process according to claim 2, wherein the second series of steps comprises at least one step for adding an enzyme preparation configured for controllably digesting the reduced-viscosity cellulosic solids fraction, said enzyme preparation comprising at least one enzyme selected from the group consisting of endo-$\beta$-1,4-glucanases, cellobiohydrolases, cellulases, hemicellulases, $\beta$-glucosidases, $\beta$-xylosidases, xylanases, $\alpha$-amylases, $\beta$-amylases, pullulases, and esterases.

4. A modular biorefining process according to claim 3, wherein the second series of steps additionally comprises steps for post-digestion recovery and recycling of a portion of the enzyme preparation.

5. A modular biorefining process according to claim 1, additionally provided with a fifth processing module comprising an anaerobic digestion module configured for receiving and processing therein said first semi-solid waste material into at least a collectable biogas and a liquid effluent.

6. A modular biorefining process according to claim 1, wherein the second processing module additionally comprises steps for recovering at least a portion of the first class of lignin derivatives.

7. A modular biorefining process according to claim 1, wherein the second series of steps comprises de-lignification of the cellulosic solids stream by one of an elemental chlorine-free (ECF) bleaching process and a total chlorine-free (TCF) bleaching process, and recovering therefrom a de-lignified cellulose pulp stream.

8. A modular biorefining process according to claim 7, wherein the second series of steps comprises a TCF bleaching process and includes at least the steps of:

washing the cellulosic solids stream with a mild alkali solution at a temperature ranging from about 60° C. to about 80° C. in a vessel pressurized with oxygen, followed by washing with water;

then washing the cellulosic solids stream with at least two washes with hydrogen peroxide, each wash followed by washing with water; and recovering the de-lignified cellulose pulp stream.

9. A modular biorefining process according to claim 1, additionally comprising a step configured for decrystallizing cellulose from the de-lignified cellulose solids fraction.

10. A modular biorefining process according to claim 1, wherein the cellulose is decrystallized by commingling with at least one of phosphoric acid, trifloroacetic acid, monoethylamine, sodium hydroxide, ionic liquids.

11. A modular biorefining process according to claim 1, wherein the fourth processing module is additionally provided with steps for recovering from the processed third liquid fraction, one or more of an acetic acid-containing liquid fraction, a fourth class of lignin derivatives, a sugar syrup, and a semi-solid waste material.

* * * * *